United States Patent
Middleton et al.

(10) Patent No.: US 11,242,557 B2
(45) Date of Patent: *Feb. 8, 2022

(54) METHODS AND COMPOSITIONS FOR STABILIZING NUCLEIC ACID-NUCLEOTIDE-POLYMERASE COMPLEXES

(71) Applicant: Omniome, Inc., San Diego, CA (US)

(72) Inventors: Morassa Mohseni Middleton, San Diego, CA (US); Mark C. Wallen, San Diego, CA (US); Pinar Iyidogan, San Diego, CA (US); Michael James Schmidt, San Diego, CA (US); Brittany A. Rohrman, La Jolla, CA (US); Ying Lin Liu, San Diego, CA (US); Fabian Block, San Diego, CA (US); Arnold Oliphant, Morgan Hill, CA (US)

(73) Assignee: OMNIOME, INC., San Diego, CA (US)

( * ) Notice: Subject to any disclaimer, the term of this patent is extended or adjusted under 35 U.S.C. 154(b) by 110 days.

This patent is subject to a terminal disclaimer.

(21) Appl. No.: 16/516,808

(22) Filed: Jul. 19, 2019

(65) Prior Publication Data

US 2019/0345544 A1 Nov. 14, 2019

Related U.S. Application Data

(63) Continuation of application No. 16/355,361, filed on Mar. 15, 2019, now Pat. No. 10,400,272.

(60) Provisional application No. 62/662,888, filed on Apr. 26, 2018.

(51) Int. Cl.
*C12Q 1/6832* (2018.01)
*C12Q 1/6816* (2018.01)

(52) U.S. Cl.
CPC ......... *C12Q 1/6832* (2013.01); *C12Q 1/6816* (2013.01)

(58) Field of Classification Search
None
See application file for complete search history.

(56) References Cited

U.S. PATENT DOCUMENTS

| | | | |
|---|---|---|---|
| 7,057,026 B2 | 6/2006 | Barnes et al. | |
| 7,211,414 B2 | 5/2007 | Hardin et al. | |
| 7,315,019 B2 | 1/2008 | Turner et al. | |
| 7,329,492 B2 | 2/2008 | Hardin et al. | |
| 7,405,281 B2 | 7/2008 | Xu et al. | |
| 7,482,120 B2 | 1/2009 | Buzby | |
| 7,544,794 B1 | 6/2009 | Benner et al. | |
| 7,956,171 B2 | 6/2011 | Siddiqi et al. | |
| 8,034,923 B1 | 10/2011 | Benner et al. | |
| 8,071,755 B2 | 12/2011 | Efcavitch et al. | |
| 8,808,989 B1 | 8/2014 | Siddiqi et al. | |
| 9,399,798 B2 | 7/2016 | Morris et al. | |
| 9,650,671 B2 | 5/2017 | Fedorov et al. | |
| 9,932,631 B1 | 4/2018 | Dambacher et al. | |
| 9,951,385 B1 | 4/2018 | Vijayan et al. | |
| 10,077,470 B2 | 9/2018 | Vijayan et al. | |
| 10,161,003 B2 | 12/2018 | Stromberg et al. | |
| 2008/0108082 A1 | 5/2008 | Rank et al. | |
| 2014/0057339 A1* | 2/2014 | Esfandyarpour | G01N 33/5438 435/287.2 |
| 2015/0203908 A1 | 7/2015 | Fedorov et al. | |
| 2015/0284788 A1* | 10/2015 | Fang | C12Q 1/6869 506/2 |
| 2017/0132361 A1 | 5/2017 | Liang et al. | |
| 2017/0314064 A1 | 11/2017 | Iyidogan et al. | |
| 2018/0044727 A1 | 2/2018 | Vijayan et al. | |
| 2018/0187245 A1 | 7/2018 | Dambacher et al. | |
| 2018/0208983 A1 | 7/2018 | Dambacher et al. | |
| 2019/0048404 A1 | 2/2019 | Dambacher | |

FOREIGN PATENT DOCUMENTS

| | | |
|---|---|---|
| WO | 9106678 | 5/1991 |
| WO | 2004018497 | 3/2004 |
| WO | 2007123744 | 11/2007 |
| WO | 2017184996 | 10/2017 |

OTHER PUBLICATIONS

U.S. Appl. No. 16/355,361, "Notice of Allowance", dated Jul. 9, 2019, 10 pages.
Bentley et al., "Accurate Whole Human Genome Sequencing Using Reversible Terminator Chemistry", Nature, vol. 456, No. 7218, Nov. 6, 2008, pp. 53-59.
PCT/US2019/022540, "International Search Report and Written Opinion", May 3, 2019, 11 pages.
PCT/US2019/022540, "International Preliminary Report on Patentability", Nov. 5, 2020, 8 pages.

* cited by examiner

*Primary Examiner* — Samuel C Woolwine
(74) *Attorney, Agent, or Firm* — Kilpatrick Townsend & Stockton LLP

(57) ABSTRACT

Methods, compositions, kits and apparatuses that include a fluid, the fluid containing a ternary complex and $Li^+$, wherein the ternary complex includes a primed template nucleic acid, a polymerase, and a nucleotide cognate for the next correct base for the primed template nucleic acid molecule. As an alternative or addition to $Li^+$, the fluid can contain betaine or a metal ion that inhibits polymerase catalysis such as $Ca^{2+}$. In addition to $Li^+$, the fluid can contain polyethylenimine (PEI) with or without betaine.

15 Claims, 20 Drawing Sheets

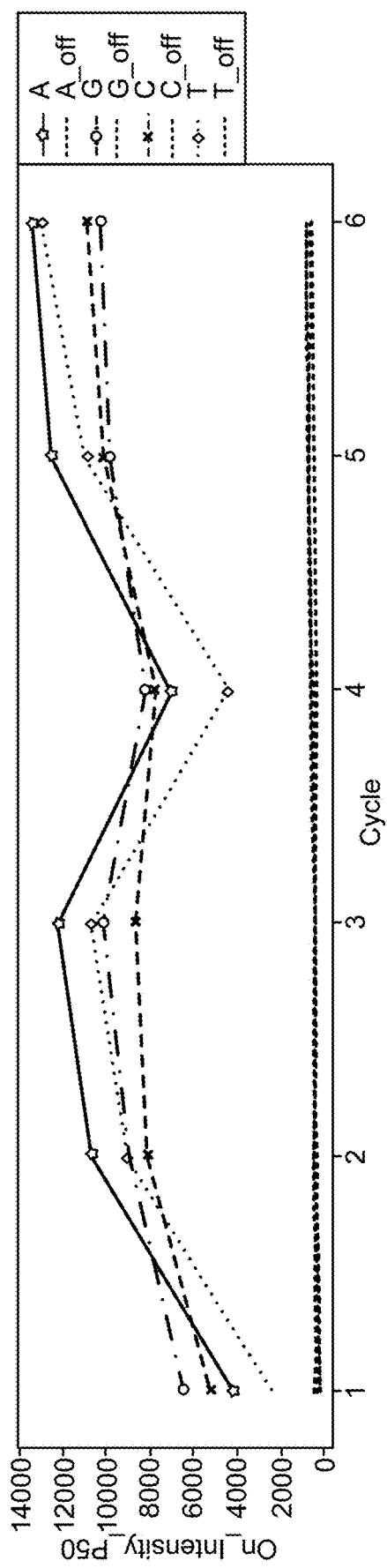

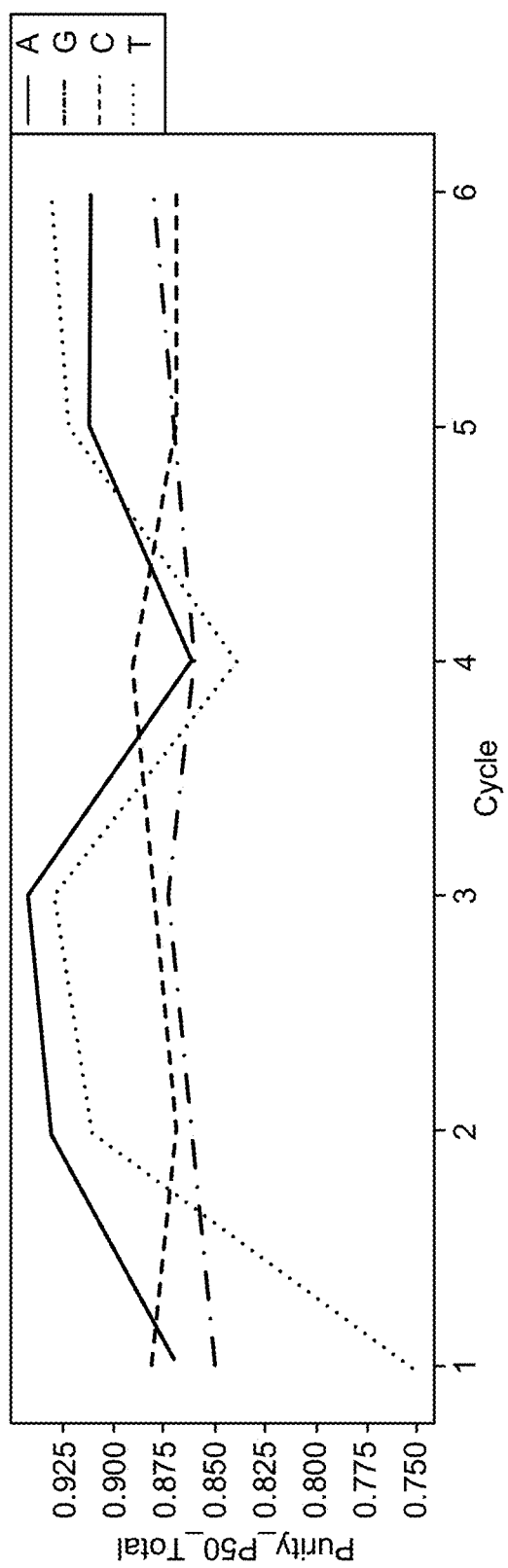

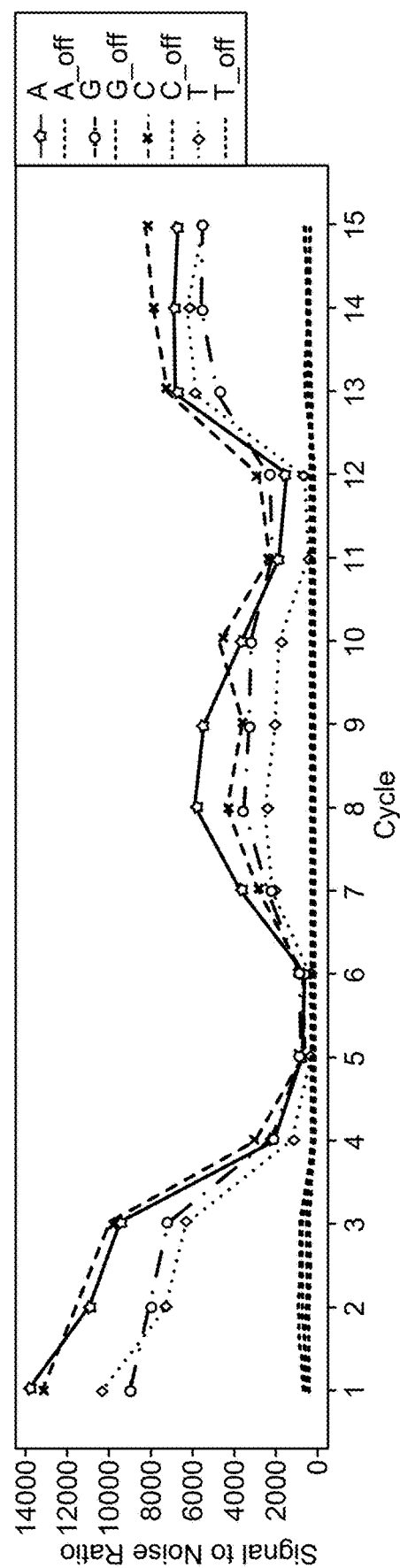

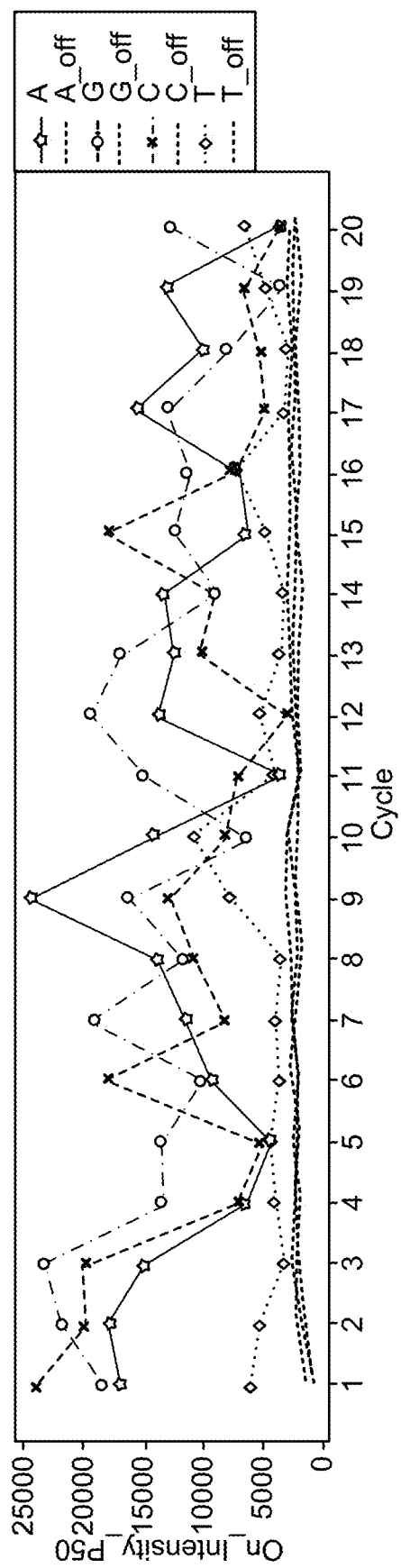

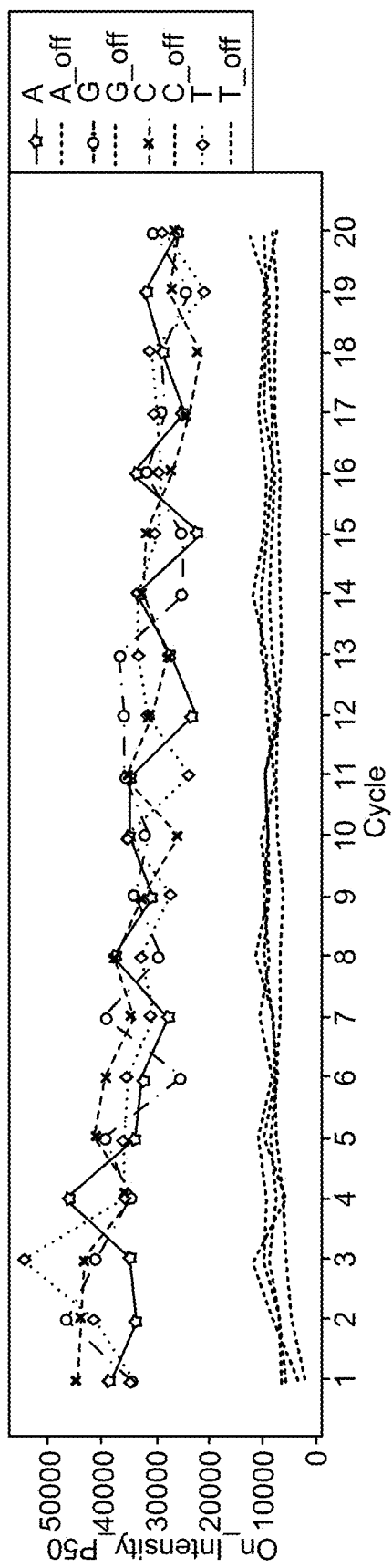

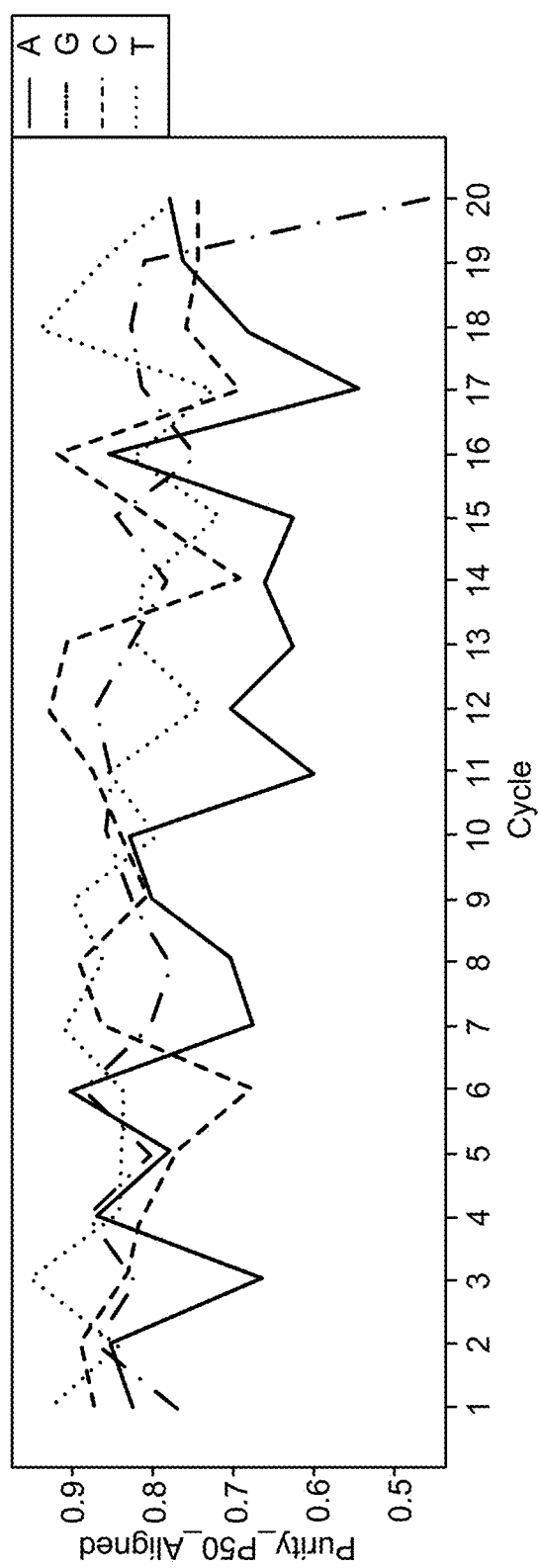

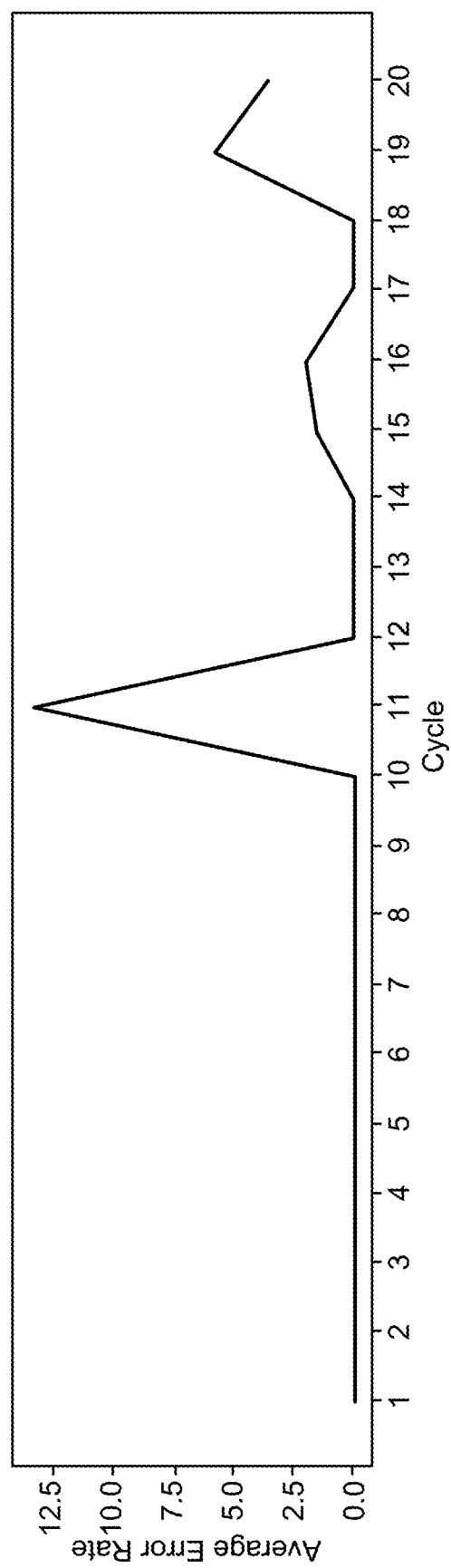

METHODS AND COMPOSITIONS FOR STABILIZING NUCLEIC ACID-NUCLEOTIDE-POLYMERASE COMPLEXES

CROSS REFERENCE TO RELATED APPLICATION

This application is a continuation of U.S. application Ser. No. 16/355,361, filed on Mar. 15, 2019, which claims the benefit of U.S. Provisional Application No. 62/662,888, filed Apr. 26, 2018, the contents of which are incorporated herein by reference in its entirety.

BACKGROUND

The present disclosure relates generally to capture, detection and sequencing of nucleic acids. More specifically, the disclosure relates to formation and detection of ternary complexes that each include a primed template nucleic acid, polymerase, and cognate nucleotide, for example, in a Sequencing By Binding™ (SBB™) method. SBB™ technology employs transient binding of a polymerase and cognate nucleotide to a primed template nucleic acid as a means to identify the template base that is at the end of the primer. Serial steps of extending the primer and detecting the next template base allow the sequence of the template to be determined. Exemplary SBB™ techniques are disclosed, for example, in commonly owned U.S. Pat. App. Pubs. 2017/0022553 A1 and 2018/0044727 A1; and U.S. patent application Ser. No. 15/873,343 (published as US 2018/0208983 A1) and Ser. No. 15/851,383 (published as US 2018/0187245 A1), each of which is incorporated herein by reference.

A difficulty of SBB™ technology is that a ternary complex is an equilibrium binding product. An equilibrium binding product coexists in solution with non-bound binding partners. Removal of non-bound binding partners from an equilibrium reaction causes the binding product to dissociate. When using labeled nucleotides in the SBB™ procedure, non-bound, labeled nucleotide provides a desired function of maintaining the equilibrium that, in turn, maintains the ternary complex. However, the non-bound, labeled nucleotide undesirably produces background signal that can obscure detection of the ternary complex. A similar difficulty can arise when using labeled polymerase in lieu of labeled nucleotides.

What is needed is a method to maintain detectable levels of ternary complexes while decreasing the concentration of labeled background components. The present invention satisfies this need and provides related advantages as well.

BRIEF SUMMARY

The present disclosure provides methods, compositions, kits and apparatuses that include a fluid, the fluid containing a ternary complex and $Li^+$, wherein the ternary complex includes a primed template nucleic acid, a polymerase, and a nucleotide cognate for the next correct base for the primed template nucleic acid molecule. As an alternative or addition to $Li^+$, the fluid can contain betaine and/or a metal ion that inhibits polymerase catalysis such as $Ca^{2+}$. In addition to $Li^+$, the fluid can contain polyethylenimine (PEI) with or without betaine.

Also provided is a method of detecting a primed template nucleic acid that includes the steps of (a) providing a fluid containing a ternary complex and $Li^+$, wherein the ternary complex includes a primed template nucleic acid, a polymerase, and a nucleotide cognate for the next correct base for the primed template nucleic acid molecule; and (b) detecting the ternary complex while it is in the fluid containing the $Li^-$. Optionally, the method further includes a step of (c) identifying the next correct base for the primed template nucleic acid molecule from the result of step (d). As an alternative or addition to $Li^+$, the fluid can contain betaine and/or an inhibitory metal ion such as $Ca^{2+}$. In addition to $Li^+$, the fluid can contain PEI with or without betaine.

A method of detecting a primed template nucleic acid can include the steps of: (a) providing a mixture that includes a ternary complex, the ternary complex including a primed template nucleic acid, a polymerase, and a nucleotide cognate for the next base of the primed template nucleic acid, wherein the mixture further includes excess polymerase of the same type present in the ternary complex and excess nucleotide of the same type present in the ternary complex; (b) replacing the excess polymerase and the excess nucleotide with a fluid containing $Li^+$; and (c) detecting the ternary complex while it is in contact with the fluid containing $Li^+$. Optionally, the method further includes a step of (d) identifying the next correct base for the primed template nucleic acid molecule from the result of step (c). As an alternative or addition to $Li^+$, the fluid can contain betaine and/or an inhibitory metal ion such as $Ca^{2+}$. In addition to $Li^-$, the fluid can contain PEI with or without betaine.

In some embodiments, a method of the present disclosure can include a step of extending a primer. For example, a method of detecting a primed template nucleic acid can include the steps of: (a) providing a fluid containing a ternary complex and $Li^+$, wherein the ternary complex includes a primed template nucleic acid, a polymerase, and a nucleotide cognate for the next correct base for the primed template nucleic acid molecule; (b) detecting the ternary complex while it is in the fluid containing the $Li^-$, (c) identifying the next correct base for the primed template nucleic acid molecule from the result of step (b); and (d) extending the primer of primed template nucleic acid. Optionally, the method can further include a step of (e) repeating steps (a) through (d) using the primed template nucleic acid having the extended primer in place of the primed template nucleic acid. As an alternative or addition to $Li^+$, the fluid can contain betaine and/or an inhibitory metal ion such as $Ca^{2+}$. In addition to $Li^+$, the fluid can contain PEI with or without betaine.

In another example of a method that includes a primer extension step, the steps of the method can include: (a) providing a mixture that includes a ternary complex, the ternary complex including a primed template nucleic acid, a polymerase, and a nucleotide cognate for the next base of the primed template nucleic acid, wherein the mixture further includes excess polymerase of the same type present in the ternary complex and excess nucleotide of the same type present in the ternary complex; (b) replacing the excess polymerase and the excess nucleotide with a fluid containing $Li^+$; (c) detecting the ternary complex while it is in contact with the fluid containing $Li^+$; (d) identifying the next correct base for the primed template nucleic acid molecule from the result of step (c); and (e) extending the primer of primed template nucleic acid. Optionally, the method can further include a step of (f) repeating steps (a) through (e) using the primed template nucleic acid having the extended primer in place of the primed template nucleic acid. As an alternative or addition to $Li^+$, the fluid can contain betaine and/or an inhibitory metal ion such as $Ca^{2+}$. In addition to $Li^+$, the fluid can contain PEI with or without betaine.

In yet another example of a method that includes a primer extension step, the steps of the method can include: (a) providing a mixture that includes a ternary complex, the ternary complex including a primed template nucleic acid, a polymerase, and a nucleotide cognate for the next base of the primed template nucleic acid, wherein the mixture further includes excess nucleotide of the same type present in the ternary complex; (b) replacing the excess nucleotide with a fluid containing $Li^+$; (c) detecting the ternary complex while it is in contact with the fluid containing $Li^+$; (d) identifying the next correct base for the primed template nucleic acid molecule from the result of step (c); and (e) extending the primer of primed template nucleic acid. Optionally, the method can further include a step of (f) repeating steps (a) through (e) using the primed template nucleic acid having the extended primer in place of the primed template nucleic acid. As an alternative or addition to $Li^+$, the fluid can contain betaine and/or an inhibitory metal ion such as $Ca^{2+}$. In addition to $Li^+$, the fluid can contain PEI with or without betaine.

BRIEF DESCRIPTION OF THE DRAWINGS

FIG. 1A shows a plot of 'on' and 'off' signal intensities for various examination conditions.

FIG. 1B shows a plot of purity for various examination conditions.

FIG. 2 shows a plot of 'on' and 'off' signal intensities for various examination conditions.

FIG. 4A shows a plot of 'on' and 'off' signal intensities for four different base types over 20 sequencing cycles carried out in the absence of LiCl.

FIG. 4C shows a plot of 'on' and 'off' signal intensities for four different base types over 20 sequencing cycles carried out in the presence of 50 mM LiCl.

FIG. 5C shows a plot of purity for four different base types over 20 sequencing cycles carried out in the presence of 50 mM LiCl.

FIG. 7B shows a plot of average error rate over 20 sequencing cycles carried out in the presence of 5 mM LiCl.

DETAILED DESCRIPTION

Figure 3:
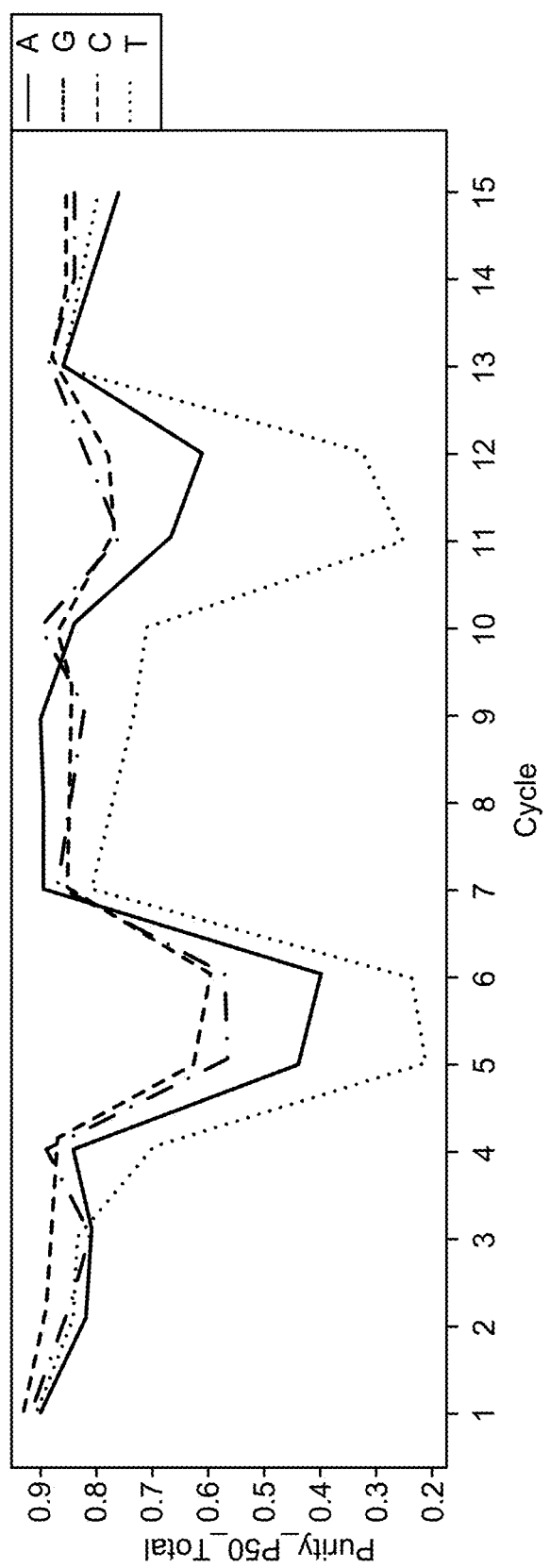
FIG. 3 shows a plot of purity for various examination conditions.

Described herein is a procedure permitting rapid and efficient identification of cognate nucleotides among members of a population of primed template nucleic acid molecules. As set forth below, this can be accomplished in different ways.

Generally, preformed ternary complexes harboring a detectable label (e.g., labeled nucleotide) can be separated from non-complexed polymerases and/or nucleotides (e.g., non-complexed labeled nucleotides or non-complexed labeled polymerases) and then imaged in the presence of a stabilizing fluid to make a nucleotide identification. The stabilizing fluid advantageously permits ternary complex detection over an extended period. It is to be understood that there are many ways in which ternary complexes can be formed, and that the manner in which the ternary complex is formed does not generally affect usefulness of the stabilizing procedure set forth herein.

Embodiments of the methods set forth herein can be used to form a reversible complex (e.g. a ternary complex) by contacting a polymerase, nucleotide and primed template nucleic acid under conditions that allow the three components to form a complex while precluding extension at the 3'-end of the primer. Extension can be precluded by a number of means set forth herein including, but not limited to, presence of a terminator moiety on the primer, presence of a polymerase inhibitor such as an inhibitory metal ion, absence of a catalytic metal ion and/or use of a polymerase variant that is inhibited from primer extension activity (e.g. due to a mutation in the catalytic domain of the polymerase). The primed template nucleic acid can be immobilized to a solid support if desired. The extent of ternary complex formation reflects an equilibrium binding condition resulting from the presence of the different binding components (i.e., polymerase and cognate nucleotide) at their associated concentrations. Although the net effect of equilibrium is that complexes that form appear to be stable during this binding step, individual complexes actually are in a state of flux. Indeed, components of the complex can be in a situation where they are continuously associating and dissociating with the blocked primed template nucleic acid molecule at equilibrium but there is no net change in concentration of free components and bound components.

Optionally, ternary complexes once formed can be contacted with a stabilizing fluid prior to detection. The stabilizing fluid can be used to change the chemical environment containing the ternary complexes. This means that the ternary complexes formed under one condition can be detected under a different condition. Although not necessarily wishing to be limited by the proposed mechanism, the stabilizing fluid can slow the dissociation of ternary complexes that otherwise occurs in the absence of one or more binding components (e.g., nucleotide and/or polymerase), thereby allowing detection of the ternary complexes over an extended timeframe. A stabilizing fluid can have other effects that improve the ability to detect or manipulate ternary complexes. For example, some stabilizing fluids can inhibit formation of binary complexes between polymerase and primed template nucleic acid (i.e. absent a cognate nucleotide) and/or otherwise act to increase the ratio of ternary complex to binary complex.

As disclosed herein, ternary complexes including a primed template nucleic acid, cognate nucleotide (optionally including a detectable label), and a polymerase (optionally including a detectable label) can be detected during or after a wash step that separates the ternary complex from non-complexed polymerase and non-complexed nucleotides. The wash step can be an imaging wash step employing an aqueous stabilizing fluid that includes a stabilizing agent that maintains the complexes (e.g., relative to the fluid lacking the stabilizing agent). Exemplary stabilizing agents include Lithium ($Li^+$), betaine, and/or an inhibitory metal ion such as $Ca^{2+}$. A particularly useful stabilizing agent includes Li+ in combination with polyethylenimine (PEI) and optionally further combined with betaine. It will be understood that $Li^+$, betaine, and other metal ions (e.g. $Ca^{2+}$) need not function as a stabilizing agent to be useful in a method or composition set forth herein. Accordingly, stabilization of ternary complexes is an optional use for these and other reagents set forth herein.

The presence of a stabilizing agent can permit removal of excess labeled components (e.g., labeled nucleotides or labeled polymerase) from a reaction vessel, while maintaining ternary complexes in the vessel for detection or other uses. Accordingly, ternary complexes immobilized within a vessel, such as a flow cell, can be washed with a stabilizing fluid and detected while in contact with the stabilizing fluid. An advantage of using the stabilizing fluid wash is that the ternary complex can be detected substantially in the absence of excess, non-complexed binding components (e.g. labeled nucleotides and/or labeled polymerase) that would undesirably increase background signals. Thus, detecting ternary complexes during a stabilizing wash step can involve detecting the complexes under changed conditions (e.g., conditions different from the equilibrium that resulted from formation of the ternary complexes). During the wash step the net forward reaction that previously lead to ternary complex formation no longer occurs or is at least substantially slowed.

Washing ternary complexes by flowing a nucleotide-free and polymerase-free stabilizing fluid through a flow cell can remove non-complexed labeled nucleotide and polymerase and reduce non-specific background signals (e.g., fluorescent background) while preserving detectability of pre-formed or existing ternary complexes. For example, ternary complexes contained within a flow cell can be detected after a period of contact with the stabilizing fluid of at least 30 seconds, 1 minute, 5 minutes, 10 minutes or longer. Alternatively or additionally, it may be desirable to detect the stabilized ternary complexes after a period of contact with the stabilizing fluid of at most 10 minutes, 5 minutes, 1 minute, 30 seconds or less.

The compositions and methods used in several embodiments set forth herein exploit the binding specificity of a ternary complex that includes a polymerase, a primed template nucleic acid, and a cognate nucleotide. This specificity can be used to identify the next correct nucleotide for the primed template nucleic acid by identifying the nucleotide present in the ternary complex. By this approach, blocking the primer from extension at its 3'-end, and then detecting formation of a ternary complex while precluding phosphodiester bond formation, optionally under equilibrium binding conditions, can occur in the same reaction mixture and without intervening reagent exchange or wash steps. Alternatively, formation of a ternary complex can be detected during an imaging wash step when excess nucleotides and polymerase have been removed from the system. The optional presence of catalytic metal ions during formation and examination of ternary complexes can mimic a more natural ternary complex condition, and so provides an added benefit over methods that omit or replace catalytic ions. The aggregated result is increased speed of single nucleotide identification (e.g. in a genotyping procedure or single sequencing cycle) and sequence identification (e.g. in a cyclic process using repeated cycles of cognate nucleotide identification and primer extension).

The present disclosure exemplifies and describes several aspects of ternary complex stabilization in the context of a Sequencing By Binding™ technique. It will be understood that the compositions and methods set forth herein need not be limited to nucleic acid sequencing. For example, this disclosure provides methods for interrogating a single nucleotide site in a primed template nucleic acid. Interrogation of a single nucleotide site can be useful for detecting a variant at a single site (e.g., a single nucleotide polymorphism or SNP), for example, in a genotyping method. Typically, a genotyping method is carried out using a template nucleic acid with a known genetic locus, but for which an allelic variation at the locus is to be determined. Alternatively, identification of a single nucleotide site can be useful for evaluating characteristics of a target polymerase, such as specificity of the polymerase for binding to a correct nucleotide. Methods that interrogate only a single nucleotide site in a template nucleic acid can be carried out using a single cycle of a Sequencing By Binding™ method set forth herein. Optionally, a single nucleotide site can be interrogated using methods or reagents of the present disclosure in combination with methods or reagents set forth in commonly owned U.S. Pat. No. 9,932,631 and U.S. provisional application having Ser. No. 62/448,630, each of which is incorporated herein by reference.

Another exemplary application of the compositions and methods set forth herein is polymerase-based capture of allelic variants. The capture methods exploit the specificity with which a polymerase can form a stabilized ternary complex with a primed template and a next correct nucleotide. For example, a stabilized ternary complex can be formed between a polymerase, target allele and cognate nucleotide for the allele. Polymerase specificity allows a target allele to be separated from other nucleic acids, including for example, other alleles that differ from the target allele by a single nucleotide. For example, a ternary complex can be formed between a polymerase, a primed template encoding a target single nucleotide polymorphism (SNP) allele and a cognate nucleotide for the SNP allele. Capture of the ternary complex will result in selective capture of the SNP allele, compared to a non-target SNP allele at the same locus, because the cognate nucleotide is selective for the target SNP when forming a ternary complex with the polymerase. Use of a stabilizing agent can be used to improve these capture methods and methods set forth in U.S. patent application Ser. No. 15/701,358, now published as US Pat. App. Pub. No. 2018/0208922 A1, which is incorporated herein by reference.

Terms used herein will be understood to take on their ordinary meaning in the relevant art unless specified otherwise. Several terms used herein, and their meanings, are set forth below.

As used herein, the term "array" refers to a population of molecules that are attached to one or more solid supports such that the molecules at one feature can be distinguished from molecules at other features. An array can include different molecules that are each located at different addressable features on a solid support. Alternatively, an array can include separate solid supports each functioning as a feature that bears a different molecule, wherein the different molecules can be identified according to the locations of the solid supports on a surface to which the solid supports are attached, or according to the locations of the solid supports in a liquid such as a fluid stream. The molecules of the array can be, for example, nucleotides, nucleic acid primers, nucleic acid templates, primed nucleic acid templates or nucleic acid enzymes such as polymerases, ligases, exonucleases or combinations thereof.

As used herein, the term "betaine" means a zwitterionic molecule having charge-separated forms with an onium atom which bears no hydrogen atoms and that is not adjacent to the anionic atom. The anionic atom can be a carboxylate group. An ammonium betaine has a cationic functional group that includes a quaternary ammonium. A particularly useful ammonium betaine is N,N,N-trimethylglycine (TMG). A phosphonium betaine has a cationic functional group that includes a phosphonium cation.

As used herein, the term "binary complex" refers to an intermolecular association between a polymerase and a primed template nucleic acid, exclusive of a nucleotide molecule such as a next correct nucleotide of the primed template nucleic acid.

As used herein, the term "blocking moiety," when used in reference to a nucleotide, means a part of the nucleotide that inhibits or prevents the 3' oxygen of the nucleotide from forming a covalent linkage to a next correct nucleotide during a nucleic acid polymerization reaction. The blocking moiety of a "reversible terminator" nucleotide can be removed from the nucleotide analog, or otherwise modified, to allow the 3'-oxygen of the nucleotide to covalently link to a next correct nucleotide. This process is referred to as "deblocking" the nucleotide analog. Such a blocking moiety is referred to herein as a "reversible terminator moiety." Exemplary reversible terminator moieties are set forth in U.S. Pat. Nos. 7,427,673; 7,414,116; 7,057,026; 7,544,794 or 8,034,923; or PCT publications WO 91/06678 or WO 07/123744, each of which is incorporated herein by reference. A nucleotide that has a blocking moiety or reversible terminator moiety can be at the 3' end of a nucleic acid, such as a primer, or can be a monomer that is not covalently attached to a nucleic acid.

As used herein, the term "catalytic metal ion" refers to a metal ion that facilitates phosphodiester bond formation between the 3'-OH of a nucleic acid (e.g., a primer) and the phosphate of an incoming nucleotide by a polymerase. A "divalent catalytic metal cation" is a catalytic metal ion having a valence of two. Catalytic metal ions can be present at concentrations that stabilize formation of a complex between a polymerase, nucleotide, and primed template nucleic acid, referred to as non-catalytic concentrations of a metal ion insofar as phosphodiester bond formation does not occur. Catalytic concentrations of a metal ion refer to the amount of a metal ion sufficient for polymerases to catalyze the reaction between the 3'-OH group of a nucleic acid (e.g., a primer) and the phosphate group of an incoming nucleotide.

The term "comprising" is intended herein to be open-ended, including not only the recited elements, but further encompassing any additional elements.

As used herein, the terms "cycle" or "round," when used in reference to a sequencing procedure, refer to the portion of a sequencing run that is repeated to indicate the presence of a nucleotide. Typically, a cycle or round includes several steps such as steps for delivery of reagents, washing away unreacted reagents and detection of signals indicative of changes occurring in response to added reagents.

As used herein, the term "diffusional exchange," when used in reference to members of a binding complex, refers to the ability of the members to move in a fluid to associate with, or dissociate from, each other. Diffusional exchange can occur when there are no barriers that prevent the members from interacting with each other to form a complex. However, diffusional exchange is understood to exist even if diffusion is retarded, reduced or altered so long as access is not absolutely prevented.

As used herein, the term "each," when used in reference to a collection of items, is intended to identify an individual item in the collection but does not necessarily refer to every item in the collection. Exceptions can occur if explicit disclosure or context clearly dictates otherwise.

As used herein, "equilibrium" refers to a state of balance due to the equal action of opposing forces. For example, a ternary complex formed between a primed template nucleic acid, polymerase, and cognate nucleotide is in equilibrium with non-bound polymerase and cognate nucleotide when the rate of formation of the ternary complex is balanced by the rate of its dissolution. Under this condition, the reversible binding reaction ceases to change its net ratio of products to reactants. If the rate of a forward reaction (e.g., ternary complex formation) is balanced by the rate of a reverse reaction (e.g., ternary complex dissociation), then there is no net change.

As used herein, the term "excess," when used in reference to components that are capable of forming a complex in a binding reaction, refers to components that are not in a bound state. Taking as an example, a reaction that forms a ternary complex, polymerases or nucleotides that are free in solution in the reaction vessel with the ternary complex are excess polymerases and nucleotides.

As used herein, the term "exogenous," when used in reference to a moiety of a molecule, means a chemical moiety that is not present in a natural analog of the molecule. For example, an exogenous label of a nucleotide is a label that is not present on a naturally occurring nucleotide. Similarly, an exogenous label that is present on a polymerase is not found on the polymerase in its native milieu.

As used herein, the term "extension," when used in reference to a nucleic acid, means a process of adding at least one nucleotide to the 3' end of the nucleic acid. The term "polymerase extension," when used in reference to a nucleic acid, refers to a polymerase catalyzed process of adding at least one nucleotide to the 3' end of the nucleic acid. A nucleotide or oligonucleotide that is added to a nucleic acid by extension is said to be incorporated into the nucleic acid. Accordingly, the term "incorporating" can be used to refer to the process of joining a nucleotide or oligonucleotide to the 3' end of a nucleic acid by formation of a phosphodiester bond.

As used herein, the term "extendable," when used in reference to a nucleotide, means that the nucleotide has an oxygen or hydroxyl moiety at the 3' position, and is capable of forming a covalent linkage to a next correct nucleotide if and when incorporated into a nucleic acid. An extendable nucleotide can be at the 3' position of a primer or it can be a monomeric nucleotide. A nucleotide that is extendable will lack blocking moieties such as reversible terminator moieties.

As used herein, the term "feature," when used in reference to an array, means a location in an array where a particular molecule is present. A feature can contain only a single molecule or it can contain a population of several molecules of the same species (i.e. an ensemble of the molecules). Alternatively, a feature can include a population of molecules that are different species (e.g. a population of ternary complexes having different template sequences). Features of an array are typically discrete. The discrete features can be contiguous or they can have spaces between each other. An array useful herein can have, for example, features that are separated by less than 100 microns, 50 microns, 10 microns, 5 microns, 1 micron, or 0.5 micron. Alternatively or additionally, an array can have features that are separated by greater than 0.5 micron, 1 micron, 5 microns, 10 microns, 50 microns or 100 microns. The features can each have an area of less than 1 square millimeter, 500 square microns, 100 square microns, 25 square microns, 1 square micron or less.

As used herein, the term "label" refers to a molecule or moiety thereof that provides a detectable characteristic. The detectable characteristic can be, for example, an optical signal such as absorbance of radiation, luminescence or fluorescence emission, luminescence or fluorescence lifetime, luminescence or fluorescence polarization, or the like; Rayleigh and/or Mie scattering; binding affinity for a ligand or receptor; magnetic properties; electrical properties; charge; mass; radioactivity or the like. Exemplary labels include, without limitation, a fluorophore, luminophore, chromophore, nanoparticle (e.g., gold, silver, carbon nanotubes), heavy atoms, radioactive isotope, mass label, charge label, spin label, receptor, ligand, or the like.

As used herein, the term "next correct nucleotide" refers to the nucleotide type that will bind and/or incorporate at the 3' end of a primer to complement a base in a template strand to which the primer is hybridized. The base in the template strand is referred to as the "next base" and is immediately 5' of the base in the template that is hybridized to the 3' end of the primer. The next correct nucleotide can be referred to as the "cognate" of the next base and vice versa. Cognate nucleotides that interact specifically with each other in a ternary complex or in a double stranded nucleic acid are said to "pair" with each other. A nucleotide having a base that is not complementary to the next template base is referred to as an "incorrect", "mismatch" or "non-cognate" nucleotide.

As used herein, the term "inhibitory metal ion" refers to a metal ion that, when in the presence of a polymerase enzyme, inhibits phosphodiester bond formation needed for chemical incorporation of a nucleotide into a primer. An inhibitory metal ion may interact with a polymerase, for example, via competitive binding compared to catalytic metal ions. A "divalent inhibitory metal ion" is an inhibitory metal ion having a valence of two. Examples of divalent inhibitory metal ions include, but are not limited to, $Ca^{2+}$, $Zn^{2+}$, $Co^{2+}$, $Ni^{2+}$, and $Sr^{2+}$. The trivalent $Eu^{3+}$ and $Tb^{3+}$ ions are inhibitory metal ions having a valence of three.

As used herein, the term "nucleotide" can be used to refer to a native nucleotide or analog thereof. Examples include, but are not limited to, nucleotide triphosphates (NTPs) such as ribonucleotide triphosphates (rNTPs), deoxyribonucleotide triphosphates (dNTPs), or non-natural analogs thereof such as dideoxyribonucleotide triphosphates (ddNTPs) or reversibly terminated nucleotide triphosphates (rtNTPs).

As used herein, the term "polyethylenimine" or "PEI" refers to a polymer with repeating unit composed [$NCH_2CH_2$]$_n$. Linear polyethyleneimines contain all secondary amines (i.e. [$NHCH_2CH_2$]$_n$), in contrast to branched PEIs which contain primary, secondary and/or tertiary amino groups. The polymer can be in a polycationic form. Polyethylenimine is also known in the art as poly(iminoethylene), polyaziridine, or poly[imino(1,2-ethanediyl)].

As used herein, the term "polymerase" can be used to refer to a nucleic acid synthesizing enzyme, including but not limited to, DNA polymerase, RNA polymerase, reverse transcriptase, primase and transferase. Typically, the polymerase has one or more active sites at which nucleotide binding and/or catalysis of nucleotide polymerization may occur. The polymerase may catalyze the polymerization of nucleotides to the 3' end of the first strand of the double stranded nucleic acid molecule. For example, a polymerase catalyzes the addition of a next correct nucleotide to the 3' oxygen group of the first strand of the double stranded nucleic acid molecule via a phosphodiester bond, thereby covalently incorporating the nucleotide to the first strand of the double stranded nucleic acid molecule. Optionally, a polymerase need not be capable of nucleotide incorporation under one or more conditions used in a method set forth herein. For example, a mutant polymerase may be capable of forming a ternary complex but incapable of catalyzing nucleotide incorporation.

As used herein, the term "primed template nucleic acid" refers to a nucleic acid hybrid having a double stranded region such that one of the strands has a 3'-end that can be extended by a polymerase. The two strands can be parts of a contiguous nucleic acid molecule (e.g. a hairpin structure) or the two strands can be separable molecules that are not covalently attached to each other.

As used herein, the term "primer" refers to a nucleic acid having a sequence that binds to a nucleic acid at or near a template sequence. Generally, the primer binds in a configuration that allows replication of the template, for example, via polymerase extension of the primer. The primer can be a first portion of a nucleic acid molecule that binds to a second portion of the nucleic acid molecule, the first portion being a primer sequence and the second portion being a primer binding sequence (e.g. a hairpin primer). Alternatively, the primer can be a first nucleic acid molecule that binds to a second nucleic acid molecule having the template sequence (e.g. a dissociable primer). A primer can consist of DNA, RNA or analogs thereof.

As used herein, a "reaction vessel" is a container that isolates one reagent or reaction (e.g., a binding reaction; an incorporation reaction; etc.) from another, or that provides a space in which a reaction can take place. Non-limiting examples of reaction vessels useful in connection with the disclosed technique include: flow cells, wells of a multiwell plate; microscope slides; open tubes (e.g., capillary tubes); closed tubes (e.g. microcentrifuge tubes, test tubes or Eppendorf Tubes™); etc. Features to be monitored during binding and/or incorporation reactions can be contained within the reaction vessel.

As used herein, the term "solid support" refers to a rigid substrate that is insoluble in aqueous liquid. The substrate can be non-porous or porous. The substrate can optionally be capable of taking up a liquid (e.g. due to porosity) but will typically be sufficiently rigid that the substrate does not swell substantially when taking up the liquid and does not contract substantially when the liquid is removed by drying. A nonporous solid support is generally impermeable to liquids or gases. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor®, silica or silica-based materials including silicon and modified silicon, carbon, metals, inorganic glasses, optical fiber bundles, and polymers.

As used herein, the term "ternary complex" refers to an intermolecular association between a polymerase, a double stranded nucleic acid and a nucleotide. Typically, the polymerase facilitates interaction between a next correct nucleotide and a template strand of the primed nucleic acid. A next correct nucleotide can interact with the template strand via Watson-Crick hydrogen bonding. The term "stabilized ternary complex" means a ternary complex having promoted or prolonged existence or a ternary complex for which disruption has been inhibited. Generally, stabilization of the ternary complex prevents covalent incorporation of the nucleotide component of the ternary complex into the primed nucleic acid component of the ternary complex.

As used herein, the term "type" or "species" is used to identify molecules that share the same chemical structure. For example, a mixture of nucleotides can include several dCTP molecules. The dCTP molecules will be understood to be the same type (or species) of nucleotide as each other, but a different type (or species) of nucleotide compared to dATP, dGTP, dTTP etc. Similarly, individual DNA molecules that have the same sequence of nucleotides are the same type (or species) of DNA, whereas DNA molecules with different sequences are different types (or species) of DNA. The term "type" or "species" can also identify moieties that share the same chemical structure. For example, the cytosine bases in a template nucleic acid will be understood to have the same type (or species) of base as each other independent of their position in the template sequence.

The embodiments set forth below and recited in the claims can be understood in view of the above definitions.

The present disclosure provides a method of detecting a primed template nucleic acid. The method can include the steps of: (a) providing a mixture that includes a ternary complex, the ternary complex including a primed template nucleic acid, a polymerase, and a nucleotide cognate for the next base of the primed template nucleic acid, wherein the mixture further includes excess polymerase of the same type present in the ternary complex and excess nucleotide of the same type present in the ternary complex; (b) replacing the excess polymerase and the excess nucleotide with a fluid containing $Li^+$ and (c) detecting the ternary complex while it is in contact with the fluid containing $Li^+$. Optionally, the method further includes a step of (d) identifying the next correct base for the primed template nucleic acid molecule from the result of step (c). As an alternative or addition to $Li^+$, the fluid can contain betaine and/or an inhibitory metal ion such as $Ca^{2+}$. In addition to $Li^+$, the fluid can contain polyethylenimine (PEI) with or without betaine.

High concentrations of detectably labeled components can be used to drive formation of transient or reversible ternary complexes that are to be detected. Unfortunately, non-complexed reagents harboring detectable labels and remaining in the presence of the specific complexes can generate signals that confound or mask the desired detection. This is especially problematic when the signal generated by the detectable label is substantially similar irrespective of whether the labeled component (e.g., polymerase or nucleotide) is free in solution or included in a complex (e.g., a ternary complex).

In particular embodiments, nucleotide concentrations substantially exceed polymerase concentrations in binding reaction mixtures and, as such, procedures employing labeled nucleotide for detection of ternary complexes can be particularly susceptible to high backgrounds that obscure ternary complex detection. Moreover, the dynamic nature of the ternary complex (e.g., where ternary complexes are in a state of flux, forming and dissociating, and exchanging with components in their chemical environments) can complicate examination of the ternary complex product when conventional aqueous wash steps are performed to remove non-complexed reagents from the system. This is because the reversible complex that is to be detected can be unstable over a time period that is used to examine or monitor the ternary complex.

Two technical issues impact detection of multicomponent complexes when using components that include detectable labels. First, signals originating from the labeled non-bound components can undesirably obscure detection of specific complexes. Second, conventional washing to remove one or more components from the system can promote dissociation of the reversible complexes that are to be detected. Each of these can be a liability when gathering sequencing data.

The importance of maintaining stability of a bound complex while detecting the complex can be appreciated in the context of array-based applications, where multiple images are acquired along the surface of the array. For example, a flow cell can include an array having a surface area greater than a single field of view for an optical imaging system. As a consequence, an optical system may acquire images of different parts of the array by a scanning or stepping process. If transient complexes to be monitored are unstable, then it is possible that lower quality data will be acquired for the later images compared to earlier images. As set forth herein, this problem can be overcome by stabilizing complexes under a condition that permits acquisition of data with high signal-to-background ratios.

A particularly useful agent for use in a method or composition of the present disclosure, for example, for stabilizing a ternary complex is lithium. Like the other alkali metals, lithium has a single valence electron that is easily given up to form a cation ($Li^+$). Lithium can be supplied to a reaction in salt form, for example, in the form of LiCl. Lithium, when in contact with ternary complex, can be at a concentration of at least 5 mM, 10 mM, 25 mM, 50 mM, 100 mM, 250 mM or higher. Alternatively or additionally, lithium can be present at a concentration of at most 250 mM, 100 mM, 50 mM, 25 mM, 10 mM, 5 mM or less.

Another useful agent for use in a method or composition of the present disclosure, for example, for stabilizing a ternary complex is betaine. Betaine, when in contact with ternary complex, can be at a concentration of at least 1 mM, 10 mM, 50 mM, 100 mM, 500 mM, 1 M, 2 M, 3 M, 3.5 M or higher. Alternatively or additionally, betaine can be present at a concentration of at most 3.5 M, 2 M, 1 M, 500 mM, 100 mM, 50 mM, 10 mM, 1 mM, or less. Betaine can be used in combination with $Li^+$ or in the absence of $Li^+$ to produce a stabilizing effect.

Polyethylenimine (PEI) can be used in a method or composition of the present disclosure, for example, for stabilizing a ternary complex. PEI, when in contact with a ternary complex, can be present at a concentration of at least 0.0001%, 0.001%, 0.01%, 0.05%, 0.1%, 1% or 5% (w/v). Alternatively or additionally, PEI can be present at a concentration of at most 5%, 1%, 0.1%, 0.05%, 0.01%, 0.001% or 0.0001% (w/v). PEI can be used in combination with $Li^-$ to produce a stabilizing effect on a ternary complex. In cases where PEI and $Li^+$ are used together, betaine can optionally be present as well, or betaine can be absent.

Inhibitory metal ions can also be used in a method or composition of the present disclosure, for example, as a stabilizing agent. A particularly useful inhibitory metal ion is $Ca^{2+}$. Inhibitory metal ions, when in contact with ternary complex, can be at a concentration of at least 0.1 mM, 0.5 mM, 1 mM, 5 mM, 10 mM, 25 mM, 50 mM, 100 mM, or higher. Alternatively or additionally, inhibitory metal ions can be present at a concentration of at most 100 mM, 50 mM, 25 mM, 10 mM, 5 mM, 1 mM, 0.5 mM, 0.1 mM or less. $Ca^{2+}$ can be used alone or in combination with one or more of $Li^+$, betaine and PEI.

A solution that is used for stabilizing a ternary complex, for example, a solution that contains Lithium, betaine, PEI and/or an inhibitory metal ion, can be buffered at a desired pH. For example, the pH of the solution can be at least 7.0, 7.5, 8.0, 8.1, 8.2, 8.3, 8.4, 8.5, 8.6, 8.7, 8.8, 8.9 or 9.0. Alternatively or additionally, the buffer can be selected to maintain the pH to be at most 9.0, 8.9, 8.8, 8.7, 8.6, 8.5, 8.4, 8.3, 8.2, 8.1, 8.0, 7.5, or 7.0. Useful buffers include those set forth in the Examples below or those having an appropriate pKa for the desired pH range, including for example, MOPS (pKa 7.2), BES (pKa 7.2), TES (pKa 7.5), Triethanolamine (pKa 7.8), EPPS or HEPPS (pKA 8.0), TRIS (pKa 8.1), Tricene (pKa 8.1), Glycylglycine (pKa 8.3), Bicine (pKa 8.3), TAPPS (pKa 8.4), Morpholine (pKa 8.5), N-Methyl-diethanolamine (pKa 8.5), 2-amino-2-methyl-1,3-propanediol (pKa 8.8), Diethanolamine (pKa 8.9), or AMPSO (pKa 9.1). A buffer can be present at an effective concentration for stabilizing ternary complexes, for example, between about 25 mM and 250 mM, between about 25 mM and 100 mM, between about 40 mM and 80 mM or other ranges.

A solution that is used for stabilizing a ternary complex, for example, a solution that contains Lithium, betaine, PEI and/or an inhibitory metal ion, can include a salt such as those set forth in the Examples section below. Particularly useful salts include, but are not limited to NaCl, KCl, K-acetate, $NH_4$-acetate, K-glutamate, $NH_4Cl$, or $(NH_4HSO_4)$. The salts can be present at an effective concentration for stabilizing ternary complexes including, for example, at least 10 mM, 25 mM, 50 mM, 100 mM, 250 mM or higher. Alternatively or additionally, the salt concentration can be at most 250 mM, 100 mM, 50 mM, 25 mM or 10 mM.

A solution that is used for stabilizing a ternary complex, for example, a solution that contains Lithium, betaine, PEI and/or an inhibitory metal ion, can include other components such as those that provide desired viscosity or molecular crowding. Exemplary components include for example, polysaccharides such as sucrose, Ficoll, or dextran; proteins such as lysozyme, albumin or casein; or polymers such as polyvinyl alcohol, polyethyleneglycols (PEG 2050, PEG 4600, PEG 6000, PEG 8000, PEG 20000). A viscous or molecular crowding agent can be present at a concentration of at least about 0.5%, 1%, 3%, 5%, 10% or more. Alternatively or additionally, the concentration can be at most 10%, 5%, 3%, 2%, 1% or 0.5%.

Other useful components to include in a solution for stabilizing ternary complexes include antifade or photoprotective reagents such as DABCO (1,4-diazabicyclo[2.2.2] octane), ascorbate, gallic acid or derivatives thereof. Other useful antifade and photoprotective reagents include, for example, those set forth in U.S. Pat. Nos. 7,993,895; 9,115,353; 10,036,011, each of which is incorporated herein by reference. Such reagents are particularly useful when present in solutions that are detected via optical methods such as luminescence and fluorescence. A method of this disclosure can include one or more steps for forming and detecting a ternary complex. Embodiments of the methods exploit the specificity with which a polymerase can form a stabilized ternary complex with a primed template nucleic acid and a next correct nucleotide. The next correct nucleotide can be non-covalently bound to the stabilized ternary complex, interacting with the other members of the complex solely via non-covalent interactions. Useful methods and compositions for forming a stabilized ternary complex are set forth in further detail below and in commonly owned U.S. Pat. App. Pub. Nos. 2017/0022553 A1 or 2018/0044727 A1; US Pat. App. Pub. No. 2018/0187245 A1, which claims priority to U.S. Pat. App. Ser. No. 62/440,624 or US Pat. App. Pub. No. 2018/0208983 A1, which claims priority to 62/450,397, each of which is incorporated herein by reference. Typically, formation and detection of ternary complex is separated from a step of extending the primer, for example, due to reagent exchange between the steps. However, in some embodiments the binding, detection and extension steps can occur in the same mixture.

While a ternary complex can form between a polymerase, primed template nucleic acid and next correct nucleotide in the absence of certain catalytic metal ions (e.g., $Mg^{2+}$), chemical addition of the nucleotide is inhibited in the absence of the catalytic metal ions. Low or deficient levels of catalytic metal ions, causes non-covalent sequestration of the next correct nucleotide in a stabilized ternary complex. Other methods disclosed herein also can be used to produce a stabilized ternary complex.

Optionally, a stabilized ternary complex can be formed when the primer of the primed template nucleic acid includes a blocking moiety (e.g. a reversible terminator moiety) that precludes enzymatic incorporation of an incoming nucleotide into the primer. The interaction can take place in the presence of stabilizers, whereby the polymerase-nucleic acid interaction is stabilized in the presence of the next correct nucleotide. The primer of the primed template nucleic acid optionally can be either an extendible primer, or a primer blocked from extension at its 3'-end (e.g., blocking can be achieved by the presence of a reversible terminator moiety on the 3'-end of the primer). The primed template nucleic acid, the polymerase and the cognate nucleotide are capable of forming a stabilized ternary complex when the base of the cognate nucleotide is complementary to the next base of the primed template nucleic acid.

As set forth above, conditions that favor or stabilize a ternary complex can be provided by the presence of a blocking group that precludes enzymatic incorporation of an incoming nucleotide into the primer (e.g. a reversible terminator moiety on the 3' nucleotide of the primer) or the absence of a catalytic metal ion. Other useful conditions include the presence of a ternary complex stabilizing agent such as an inhibitory metal ion (e.g., a divalent or trivalent inhibitory metal ion) that inhibits polymerase catalyzed nucleotide incorporation or polymerization. Inhibitory metal ions include, but are not limited to, calcium, strontium, scandium, titanium, vanadium, chromium, iron, cobalt, nickel, copper, zinc, gallium, germanium, arsenic, selenium, rhodium, europium, and terbium ions. Optionally, conditions that disfavor or destabilize binary complexes (i.e. complexes between polymerase and primed nucleic acid but lacking cognate nucleotide) are provided by the presence of one or more monovalent cations and/or glutamate anions. As a further example of a stabilizing condition, a polymerase engineered to have reduced catalytic activity or reduced propensity for binary complex formation can be used. Exemplary engineered polymerases are set forth in US Pat. App. Pub. Nos. 2017/0314072 A1 or 2018/0155698 A1, each of which is incorporated herein by reference.

Ternary complex stabilization conditions can accentuate the difference in affinity of polymerase toward primed template nucleic acids in the presence of different nucleotides, for example, by destabilizing binary complexes. Optionally, the conditions cause differential affinity of the polymerase for the primed template nucleic acid in the presence of different nucleotides. By way of example, the conditions include, but are not limited to, high salt and glutamate ions. For example, the salt may dissolve in aqueous solution to yield a monovalent cation, such as a monovalent metal cation (e.g., sodium ion or potassium ion). Optionally, the salt that provides the monovalent cations (e.g., monovalent metal cations) further provides glutamate ions. Optionally, the source of glutamate ions can be potassium glutamate. In some instances, the concentrations of potassium glutamate that can be used to alter polymerase affinity of the primed template nucleic acid extend from 10 mM to 1.6 M of potassium glutamate, or any amount in between 10 mM and 1.6 M. As indicated above, high salt refers to a concentration of salt from 50 mM to 1.5 M salt.

It will be understood that options set forth herein for stabilizing a ternary complex need not be mutually exclusive and instead can be used in various combinations. For example, a ternary complex can be stabilized by one or a combination of means including, but not limited to, presence of crosslinking of the polymerase domains; crosslinking of the polymerase to the nucleic acid; polymerase mutations that stabilize the ternary complex; allosteric inhibition by small molecules; presence of $Li^+$, PEI, betaine, uncompetitive inhibitors, competitive inhibitors, or non-competitive inhibitors; absence of catalytic metal ions; presence of a blocking moiety on the primer; or other means set forth herein.

Nucleic acids that are used in a method or composition herein can be DNA such as genomic DNA, synthetic DNA, amplified DNA, copy DNA (cDNA) or the like. RNA can also be used such as mRNA, ribosomal RNA, tRNA or the like. Nucleic acid analogs can also be used as templates herein. Thus, template nucleic acids used herein can be derived from a biological source, synthetic source or amplification product. Primers used herein can be DNA, RNA or analogs thereof.

Particularly useful nucleic acid templates are genome fragments that include sequences identical to a portion of a genome. A population of genome fragments can include at least 5%, 10%, 20%, 30%, or 40%, 50%, 60%, 70%, 75%, 80%, 85%, 90%, 95% or 99% of a genome. A genome fragment can have, for example, a sequence that is substantially identical to at least about 25, 50, 70, 100, 200, 300, 400, 500, 600, 700, 800, 900 or 1000 or more nucleotides of a genome. Alternatively or additionally, a genome fragment can have a sequence that is substantially identical to no more than $1 \times 10^5$, $1 \times 10^4$, $1 \times 10^3$, 800, 600, 400, 200, 100, 75, 50 or 25 nucleotides of a genome. A genome fragment can be DNA, RNA, or an analog thereof.

Exemplary organisms from which nucleic acids can be derived include, for example, those from a mammal such as a rodent, mouse, rat, rabbit, guinea pig, ungulate, horse, sheep, pig, goat, cow, cat, dog, primate, human or non-human primate; a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a *Dictyostelium discoideum*; a fungi such as *Pneumocystis carinii*, *Takifugu rubripes*, yeast, *Saccharamoyces cerevisiae* or *Schizosaccharomyces pombe*; or a *Plasmodium falciparum*. Nucleic acids can also be derived from a prokaryote such as a bacterium, *Escherichia coli*, staphylococci or *Mycoplasma pneumoniae*; an archae; a virus such as Hepatitis C virus or human immunodeficiency virus; or a viroid. Nucleic acids can be derived from a homogeneous culture or population of the above organisms or alternatively from a collection of several different organisms, for example, in a community or ecosystem. Nucleic acids can be isolated using methods known in the art including, for example, those described in Sambrook et al., *Molecular Cloning: A Laboratory Manual*, 3rd edition, Cold Spring Harbor Laboratory, New York (2001) or in Ausubel et al., *Current Protocols in Molecular Biology*, John Wiley and Sons, Baltimore, Md. (1998), each of which is incorporated herein by reference.

A template nucleic acid can be obtained from a preparative method such as genome isolation, genome fragmentation, gene cloning and/or amplification. The template can be obtained from an amplification technique such as polymerase chain reaction (PCR), rolling circle amplification (RCA), multiple displacement amplification (MDA) or the like. Exemplary methods for isolating, amplifying and fragmenting nucleic acids to produce templates for analysis on an array are set forth in U.S. Pat. Nos. 6,355,431 or 9,045,796, each of which is incorporated herein by reference. Amplification can also be carried out using a method set forth in Sambrook et al., *Molecular Cloning: A Laboratory Manual*, 3rd edition, Cold Spring Harbor Laboratory, New York (2001) or in Ausubel et al., *Current Protocols in Molecular Biology*, John Wiley and Sons, Baltimore, Md. (1998), each of which is incorporated herein by reference.

Any of a variety of polymerases can be used in a method set forth herein. Reference to a particular polymerase, such as those exemplified throughout this disclosure, will be understood to include functional variants thereof unless indicated otherwise. Particularly useful functions of a polymerase include formation of a ternary complex or catalysis of the polymerization of a nucleic acid strand using an existing nucleic acid as a template. A particular polymerase activity or characteristic set forth herein, for example, forming ternary complexes that are stabilized by a particular reagent such as $Li^+$, PEI, betaine and/or an inhibitory metal ion such as $Ca^{2-}$, can be shared by polymerases that have been grouped by known classifications. A particularly useful classification is based on structural homology such as the classification of polymerases into families identified as A, B, C, D, X, Y, and RT. DNA Polymerases in Family A include, for example, T7 DNA polymerase, eukaryotic mitochondrial DNA Polymerase γ, *E. coli* DNA Pol I, *Thermus aquaticus* Pol I, and *Bacillus stearothermophilus* Pol I. DNA Polymerases in Family B include, for example, eukaryotic DNA polymerases α, δ, and ε; DNA polymerase ζ; T4 DNA polymerase, Phi29 DNA polymerase, and RB69 bacteriophage DNA polymerase. Family C includes, for example, the *E. coli* DNA Polymerase III alpha subunit. Family B archaeon DNA polymerases include, for example, Vent, Deep Vent, Pfu and 9° N (e.g., Therminator™ DNA polymerase from New England BioLabs Inc.; Ipswich, Mass.) polymerases. Family D includes, for example, polymerases derived from the *Euryarchaeota* subdomain of *Archaea*. DNA Polymerases in Family X include, for example, eukaryotic polymerases Pol β, pol α, Pol λ, and Pol μ, and *S. cerevisiae* Pol4. DNA Polymerases in Family Y include, for example, Pol η, Pol τ, Pol κ, *E. coli* Pol IV (DINB) and *E. coli* Pol V (UmuD'2C). The RT (reverse transcriptase) family of DNA polymerases includes, for example, retrovirus reverse transcriptases and eukaryotic telomerases. Exemplary RNA polymerases include, but are not limited to, viral RNA polymerases such as T7 RNA polymerase; Eukaryotic RNA polymerases such as RNA polymerase I, RNA polymerase II, RNA polymerase III, RNA polymerase IV, and RNA polymerase V; and *Archaea* RNA polymerase.

The above classifications are provided for illustrative purposes. It will be understood that variations in the classification system are possible. For example, in at least one classification system Family C polymerases have been categorized as a subcategory of Family X. Furthermore, polymerases can be classified according to other characteristics, whether functional or structural, that may or may not overlap with the structural characteristics exemplified above. Some exemplary characteristics are set forth in further detail below.

Polymerases that may be used in a method or composition set forth herein include naturally occurring polymerases and modified variations thereof, including, but not limited to, mutants, recombinants, fusions, genetic modifications, chemical modifications, synthetics, and analogs. Useful polymerases for ternary complex formation and detection are not limited to polymerases that have the ability to catalyze a polymerization reaction. Optionally, a useful polymerase will have the ability to catalyze a polymerization reaction in at least one condition that is not used during formation or examination of a stabilized ternary complex. Optionally, a polymerase that participates in a stabilized ternary complex has modified properties, for example, enhanced binding affinity to nucleic acids, reduced binding affinity to nucleic acids, enhanced binding affinity to nucleotides, reduced binding affinity to nucleotides, enhanced specificity for next correct nucleotides, reduced specificity for next correct nucleotides, reduced catalysis rates, catalytic inactivity etc. Mutant polymerases include, for example, polymerases wherein one or more amino acids are replaced with other amino acids, or insertions or deletions of one or more amino acids. Exemplary polymerases that can be used to form a stabilized ternary complex include, for example, wild type and mutant polymerases set forth in U.S. patent application Ser. No. 15/866,353, now published as US Pat. App. Pub. No. 2018/0155698 A1, or US Pat. App. Pub. No. 2017/0314072 A1, each of which is incorporated herein by reference.

Polymerases that contain an exogenous label moiety (e.g., an exogenous fluorophore), which can be used to detect the polymerase, can be useful in some embodiments. Optionally, the label moiety can be attached after the polymerase has been at least partially purified using protein isolation techniques. For example, the exogenous label moiety can be chemically linked to the polymerase using a free sulfhydryl or a free amine moiety of the polymerase. This can involve chemical linkage to the polymerase through the side chain of a cysteine residue, or through the free amino group of the N-terminus. An exogenous label moiety can also be attached to a polymerase via protein fusion. Exemplary label moieties that can be attached via protein fusion include, for example, green fluorescent protein (GFP), phycobiliproteins (e.g. phycocyanin and phycoerythrin) or wavelength-shifted variants of GFP or phycobiliproteins. In some embodiments, an exogenous label on a polymerase can function as a member of a FRET pair. The other member of the FRET pair can be an exogenous label that is attached to a nucleotide that binds to the polymerase in a stabilized ternary complex. As such, the stabilized ternary complex can be detected or identified via FRET.

Alternatively, a polymerase that participates in a stabilized ternary complex need not be attached to an exogenous label. For example, the polymerase need not be covalently attached to an exogenous label. Instead, the polymerase can lack any label until it associates with a labeled nucleotide and/or labeled nucleic acid (e.g. labeled primer and/or labeled template).

A ternary complex that is made or used in accordance with the present disclosure may optionally include one or more exogenous label(s). The label can be attached to a component of the ternary complex (e.g. attached to the polymerase, template nucleic acid, primer and/or cognate nucleotide) prior to formation of the ternary complex. Exemplary attachments include covalent attachments or non-covalent attachments such as those set forth herein, in references cited herein or known in the art. In some embodiments, a labeled component is delivered in solution to a solid support that is attached to an unlabeled component, whereby the label is recruited to the solid support by virtue of forming a stabilized ternary complex. As such, the support-attached component can be detected or identified based on observation of the recruited label. Whether used in solution phase or on a solid support, exogenous labels can be useful for detecting a stabilized ternary complex or an individual component thereof, during an examination step. An exogenous label can remain attached to a component after the component dissociates from other components that had formed a stabilized ternary complex. Exemplary labels, methods for attaching labels and methods for using labeled components are set forth in further detail below or in commonly owned U.S. Pat. App. Pub. Nos. 2017/0022553 A1 or 2018/0044727 A1; or U.S. patent application Ser. No. 15/851,383 (published as US Pat. App. Pub. No. 2018/0187245 A1), Ser. No. 15/873, 343 (published as US Pat. App. Pub. No. 2018/0208983 A1); or US Pat. App. Pub. No. 2018/0208983 A1, which claims priority to 62/450,397 and 62/506,759, each of which is incorporated herein by reference.

As set forth above, different activities of polymerases can be exploited in a method set forth herein. A polymerase can be useful, for example, in one or both of an examination step or, as set forth in further detail below, in an extension step. The different activities can follow from differences in the structure (e.g. via natural activities, mutations or chemical modifications). Nevertheless, polymerase can be obtained from a variety of known sources and applied in accordance with the teachings set forth herein and recognized activities of polymerases. Useful DNA polymerases include, but are not limited to, bacterial DNA polymerases, eukaryotic DNA polymerases, archaeal DNA polymerases, viral DNA polymerases and phage DNA polymerases. Bacterial DNA polymerases include *E. coli* DNA polymerases I, II and III, IV and V, the Klenow fragment of *E. coli* DNA polymerase, *Clostridium stercorarium* (Cst) DNA polymerase, *Clostridium thermocellum* (Cth) DNA polymerase and *Sulfolobus solfataricus* (Sso) DNA polymerase. Eukaryotic DNA polymerases include DNA polymerases $\alpha$, $\beta$, $\gamma$, $\delta$, $\epsilon$, $\eta$, $\zeta$, $\lambda$, $\sigma$, $\mu$, and k, as well as the Rev1 polymerase (terminal deoxycytidyl transferase) and terminal deoxynucleotidyl transferase (TdT). Viral DNA polymerases include T4 DNA polymerase, phi-29 DNA polymerase, GA-1, phi-29-like DNA polymerases, PZA DNA polymerase, phi-15 DNA polymerase, Cpl DNA polymerase, Cp7 DNA polymerase, T7 DNA polymerase, and T4 polymerase. Other useful DNA polymerases include thermostable and/or thermophilic DNA polymerases such as *Thermus aquaticus* (Taq) DNA polymerase, *Thermus filiformis* (Tfi) DNA polymerase, *Thermococcus zilligi* (Tzi) DNA polymerase, *Thermus thermophilus* (Tth) DNA polymerase, *Thermus flavusu* (Tfl) DNA polymerase, *Pyrococcus woesei* (Pwo) DNA polymerase, *Pyrococcus furiosus* (Pfu) DNA polymerase and Turbo Pfu DNA polymerase, *Thermococcus litoralis* (Tli) DNA polymerase,

*Pyrococcus* sp. GB-D polymerase, *Thermotoga maritima* (Tma) DNA polymerase, *Bacillus stearothermophilus* (Bst) DNA polymerase, *Pyrococcus Kodakaraensis* (KOD) DNA polymerase, Pfx DNA polymerase, *Thermococcus* sp. JDF-3 (JDF-3) DNA polymerase, *Thermococcus gorgonarius* (Tgo) DNA polymerase, *Thermococcus acidophilium* DNA polymerase; *Sulfolobus acidocaldarius* DNA polymerase; *Thermococcus* sp. go N-7 DNA polymerase; *Pyrodictium occultum* DNA polymerase; *Methanococcus voltae* DNA polymerase; *Methanococcus thermoautotrophicum* DNA polymerase; *Methanococcus jannaschii* DNA polymerase; *Desulfurococcus* strain TOK DNA polymerase (D. Tok Pol); *Pyrococcus abyssi* DNA polymerase; *Pyrococcus horikoshii* DNA polymerase; *Pyrococcus islandicum* DNA polymerase; *Thermococcus fumicolans* DNA polymerase; *Aeropyrum pernix* DNA polymerase; and the heterodimeric DNA polymerase DP1/DP2. Engineered and modified polymerases also are useful in connection with the disclosed techniques. For example, modified versions of the extremely thermophilic marine archaea *Thermococcus species* 9° N (e.g., Therminator™ DNA polymerase from New England BioLabs Inc.; Ipswich, Mass.) can be used. Still other useful DNA polymerases, including the 3PDX polymerase are disclosed in U.S. Pat. No. 8,703,461, the disclosure of which is incorporated herein by reference.

Useful RNA polymerases include, but are not limited to, viral RNA polymerases such as T7 RNA polymerase, T3 polymerase, SP6 polymerase, and Kll polymerase; Eukaryotic RNA polymerases such as RNA polymerase I, RNA polymerase II, RNA polymerase III, RNA polymerase IV, and RNA polymerase V; and Archaea RNA polymerase.

Another useful type of polymerase is a reverse transcriptase. Exemplary reverse transcriptases include, but are not limited to, HIV-1 reverse transcriptase from human immunodeficiency virus type 1 (PDB 1HMV), HIV-2 reverse transcriptase from human immunodeficiency virus type 2, M-MLV reverse transcriptase from the Moloney murine leukemia virus, AMV reverse transcriptase from the avian myeloblastosis virus, and Telomerase reverse transcriptase that maintains the telomeres of eukaryotic chromosomes.

A polymerase having an intrinsic 3'-5' proofreading exonuclease activity can be useful for some embodiments. Polymerases that substantially lack 3'-5' proofreading exonuclease activity are also useful in some embodiments, for example, in most genotyping and sequencing embodiments. Absence of exonuclease activity can be a wild type characteristic or a characteristic imparted by a variant or engineered polymerase structure. For example, exo minus Klenow fragment is a mutated version of Klenow fragment that lacks 3'-5' proofreading exonuclease activity. Klenow fragment and its exo minus variant can be useful in a method or composition set forth herein.

A stabilized ternary complex can include a native nucleotide, nucleotide analog or modified nucleotide as desired to suit a particular application or configuration of the methods. Optionally, a nucleotide analog has a nitrogenous base, five-carbon sugar, and phosphate group, wherein any moiety of the nucleotide may be modified, removed and/or replaced as compared to a native nucleotide. Nucleotide analogs may be non-incorporable nucleotides (i.e. nucleotides that are incapable of reacting with the 3' oxygen of a primer to form a covalent linkage). Such nucleotides that are incapable of incorporation include, for example, monophosphate and diphosphate nucleotides. In another example, the nucleotide may contain modification(s) to the triphosphate group that render the nucleotide non-incorporable. Examples of non-incorporable nucleotides may be found in U.S. Pat. No. 7,482,120, which is incorporated by reference herein. In some embodiments, non-incorporable nucleotides may be subsequently modified to become incorporable. Non-incorporable nucleotide analogs include, but are not limited to, alpha-phosphate modified nucleotides, alpha-beta nucleotide analogs, beta-phosphate modified nucleotides, beta-gamma nucleotide analogs, gamma-phosphate modified nucleotides, or caged nucleotides. Further examples of nucleotide analogs are described in U.S. Pat. No. 8,071,755, which is incorporated by reference herein.

Nucleotide analogs that are used herein, for example, to participate in stabilized ternary complexes can include terminators that reversibly prevent subsequent nucleotide incorporation at the 3'-end of the primer after the analog has been incorporated into the primer. For example, U.S. Pat. Nos. 7,544,794 and 8,034,923 (the disclosures of these patents are incorporated herein by reference) describe reversible terminators in which the 3'-OH group is replaced by a 3'-ONH$_2$ moiety. Another type of reversible terminator is linked to the nitrogenous base of a nucleotide as set forth, for example, in U.S. Pat. No. 8,808,989 (the disclosure of which is incorporated herein by reference). Other reversible terminators that similarly can be used in connection with the methods described herein include those described in references cited elsewhere herein or in U.S. Pat. Nos. 7,956,171, 8,071,755, and 9,399,798 (the disclosures of these U.S. patents are incorporated herein by reference). In certain embodiments, a reversible terminator moiety can be removed from a primer, in a process known as "deblocking," allowing for subsequent nucleotide incorporation. Compositions and methods for deblocking are set forth in references cited herein in the context of reversible terminators.

Alternatively, nucleotide analogs irreversibly prevent nucleotide incorporation at the 3'-end of the primer to which they have been incorporated. Irreversible nucleotide analogs include 2', 3'-dideoxynucleotides (ddNTPs such as ddGTP, ddATP, ddTTP, ddCTP). Dideoxynucleotides lack the 3'-OH group of dNTPs that would otherwise participate in polymerase-mediated primer extension. Thus, the 3' position has a hydrogen moiety instead of the native hydroxyl moiety. Irreversibly terminated nucleotides can be particularly useful for genotyping applications or other applications where primer extension or sequential detection along a template nucleic acid is not desired.

In particular embodiments, nucleotide analogs that are used herein, for example, to participate in stabilized ternary complexes do not include blocking groups (e.g. reversible terminators) that prevent subsequent nucleotide incorporation at the 3'-end of the primer after the analog has been incorporated into the primer. This can be the case whether or not an extension step is carried out using nucleotide(s) having a blocking group (e.g. reversible terminator).

In some embodiments, a nucleotide that is used herein, for example, to participate in forming a stabilized ternary complex, can include an exogenous label. For example, an exogenously labeled nucleotide can include a reversible or irreversible terminator moiety, an exogenously labeled nucleotide can be non-incorporable, an exogenously labeled nucleotide can lack terminator moieties, an exogenously labeled nucleotide can be incorporable or an exogenously labeled nucleotide can be both incorporable and non-terminated. Exogenously labeled nucleotides can be particularly useful when used to form a stabilized ternary complex with a non-labeled polymerase. Alternatively, an exogenous label on a nucleotide can provide one partner in a fluorescence resonance energy transfer (FRET) pair and an exogenous label on a polymerase can provide the second partner of the pair. As such, FRET detection can be used to identify a stabilized ternary complex that includes both partners.

Alternatively, a nucleotide that is used herein, for example, to participate in forming a ternary complex can lack exogenous labels (i.e. the nucleotide can be "non-labeled"). For example, a non-labeled nucleotide can include a reversible or irreversible terminator moiety, a non-labeled nucleotide can be non-incorporable, a non-labeled nucleotide can lack terminator moieties, a non-labeled nucleotide can be incorporable, or a non-labeled nucleotide can be both incorporable and non-terminated. Non-labeled nucleotides can be useful when a label on a polymerase is used to detect a stabilized ternary complex or when label-free detection is used. Non-labeled nucleotides can also be useful in an extension step of a method set forth herein. It will be understood that absence of a moiety or function for a nucleotide refers to the nucleotide having no such function or moiety. However, it will also be understood that one or more of the functions or moieties set forth herein for a nucleotide, or analog thereof, or otherwise known in the art for a nucleotide, or analog thereof, can be specifically omitted in a method or composition set forth herein.

Optionally, a nucleotide (e.g. a native nucleotide or nucleotide analog) is present in a mixture during or after formation of a stabilized ternary complex. For example, at least 1, 2, 3, 4 or more nucleotide types can be present. Alternatively or additionally, at most 4, 3, 2, or 1 nucleotide types can be present. Similarly, one or more nucleotide types that are present can be complementary to at least 1, 2, 3 or 4 base types in a template nucleic acid. Alternatively or additionally, one or more nucleotide types that are present can be complementary to at most 4, 3, 2, or 1 base types in a template nucleic acid. Different base types can be identifiable by the presence of different exogenous labels on the different nucleotides. Alternatively, two or more nucleotide types can have exogenous labels that are not distinguishable. In the latter format the different nucleotides can nevertheless be distinguished due to being separately delivered to a reaction vessel or due to an encoding and decoding scheme as set forth, for example, in US patent application Ser. No. 15/922,787, published as US Pat. App. Pub. No. 2018/0305749 A1, or U.S. Pat. No. 9,951,385, each of which is incorporated herein by reference.

Any nucleotide modification that stabilizes a polymerase in a ternary complex may be used in the methods disclosed herein. The nucleotide may be bound permanently or transiently to a polymerase. Optionally, a nucleotide analog is fused to a polymerase, for example, via a covalent linker. Optionally, a plurality of nucleotide analogs is fused to a plurality of polymerases, wherein each nucleotide analog is fused to a different polymerase. Optionally, a nucleotide that is present in a stabilized ternary complex is not the means by which the ternary complex is stabilized. Accordingly, any of a variety of other ternary complex stabilization methods may be combined in a reaction utilizing a nucleotide analog.

In particular embodiments, the primer strand of a primed template nucleic acid that is present in a stabilized ternary complex is chemically unchanged by the polymerase that is present during one or more steps of a method set forth herein. For example, the primer need not be extended by formation of a new phosphodiester bond, nor shortened by nucleolytic degradation during a step for forming a stabilized ternary complex, nor during a step for detecting the stabilized ternary complex.

Particular embodiments of the methods set forth herein include a step of forming a mixture that includes several components. The components of the mixture can be delivered to a vessel in any desired order or they can be delivered simultaneously. Furthermore, some of the components can be mixed with each other to form a first mixture that is subsequently contacted with other components to form a more complex mixture. Taking as an example, a step of forming a mixture that includes a primed template nucleic acid, a polymerase and a plurality of different nucleotide types, it will be understood that the different nucleotide types in the plurality can be contacted with each other prior to being contacted with the primed template nucleic acid. Alternatively, two or more of the nucleotide types can be delivered separately to the primed template nucleic acid and/or the polymerase. As such, a first nucleotide type can be contacted with the primed template nucleic acid prior to being contacted with a second nucleotide type. Alternatively or additionally, the first nucleotide type can be contacted with the polymerase prior to being contacted with a second nucleotide type.

In particular embodiments, polymerase and nucleotides are soluble in a fluid that is used to stabilize ternary complex. For example, a stabilizing fluid can advantageously be an aqueous fluid. The stabilizing fluid can lack solvents that do not solubilize polymerase and/or nucleotides. For example, a ternary complex stabilizing fluid can be devoid of alcohols or oils that do not solubilize polymerase and/or nucleotides. Exemplary fluids that do not solubilize polymerase and/or nucleotides are set forth in U.S. patent application Ser. No. 16/164,417, which claims priority to U.S. Pat. App. Ser. No. 62/574,308, each of which is incorporated herein by reference. In some embodiments, a ternary complex stabilizing fluid can function as a wash fluid to remove non-complexed nucleotide or polymerase from an immobilized ternary complex.

A ternary complex stabilizing fluid can be devoid of one or more components of a ternary complex binding reaction prior to being contacted with a ternary complex. For example, a stabilizing fluid that contains $Li^+$, PEI, betaine or an inhibitory metal cation (e.g. $Ca^{2+}$) can be devoid of polymerase or nucleotides prior to being contacted with a ternary complex. As such, the stabilizing fluid can function as a wash to remove excess polymerase or nucleotides from a binding reaction that previously functioned to form a ternary complex. In particular embodiments, the concentration of ternary complex in a stabilization fluid is greater than the concentration of free nucleotide and/or polymerase in the fluid. The free nucleotide and polymerase in this fluid can be the same type that is present in the ternary complex. It will be understood that $Li^+$, PEI, betaine, inhibitory metal cation (e.g. $Ca^{2+}$) or other ternary complex stabilizing agent can be present during ternary complex formation. Alternatively, the ternary complex stabilizing agent can be introduced to a ternary complex that has already been formed.

A ternary complex can be detected via the presence of an exogenous label on one or more component of the complex. Examples of useful exogenous labels include, but are not limited to, radiolabel moieties, luminophore moieties, fluorophore moieties, quantum dot moieties, chromophore moieties, enzyme moieties, electromagnetic spin labeled moieties, nanoparticle light scattering moieties, and any of a variety of other signal generating moieties known in the art. Suitable enzyme moieties include, for example, horseradish peroxidase, alkaline phosphatase, beta-galactosidase, or acetylcholinesterase. Exemplary fluorophore moieties include, but are not limited to rhodols; resorufins; coumarins; xanthenes; acridines; fluoresceins; rhodamines; erythrins; cyanins; phthalaldehydes; naphthylamines; fluorescamines;

benzoxadiazoles; stilbenes; pyrenes; indoles; borapolyazaindacenes; quinazolinones; eosin; erythrosin; Malachite green; CY dyes (GE Biosciences), including Cy3 (and its derivatives) and Cy5 (and its derivatives); DYOMICS and DYLIGHT dyes (Dyomics) including DY-547, DY-630, DY-631, DY-632, DY-633, DY-634, DY-635, DY-647, DY-649, DY-652, DY-678, DY-680, DY-682, DY-701, DY-734, DY-752, DY-777 and DY-782; Lucifer Yellow; CASCADE BLUE; TEXAS RED; BODIPY (borondipyrromethene) (Molecular Probes) dyes including BODIPY 630/650 and BODIPY 650/670; ATTO dyes (Atto-Tec) including ATTO 390, ATTO 425, ATTO 465, ATTO 610 611X, ATTO 610, ATTO 635; ALEXA FLUORS including ALEXA FLUOR 633, ALEXA FLUOR 647, ALEXA FLUOR 660, ALEXA FLUOR 700, ALEXA FLUOR 750, and ALEXA FLUOR 680 (Molecular Probes); DDAO (7-hydroxy-9H-(1,3-dichloro-9,9-dimethylacridin-2-one or any derivatives thereof) (Molecular Probes); QUASAR dyes (Biosearch); IRDYES dyes (LiCor) including IRDYE 700DX (NHS ester), IRDYE 800RS (NHS ester) and IRDYE 800CW (NHS ester); EVOBLUE dyes (Evotech Biosystems); JODA 4 dyes (Applied Biosystems); HILYTE dyes (AnaSpec); MR121 and MR200 dyes (Roche); Hoechst dyes 33258 and 33242 (Invitrogen); FAIR OAKS RED (Molecular Devices); SUNNYVALE RED (Molecular Devices); LIGHT CYCLER RED (Roche); EPOCH (Glen Research) dyes including EPOCH REDMOND RED, EPOCH YAKIMA YELLOW, EPOCH GIG HARBOR GREEN; Tokyo green (M. Kamiya, et al., 2005 Angew. Chem. Int. Ed. 44:5439-5441); and CF dyes including CF 647 and CF555 (Biotium), and others known in the art such as those described in *Principles of Fluorescence Spectroscopy*, Joseph R. Lakowicz (Editor), Plenum Pub Corp, 2nd edition (July 1999) and the 6th Edition of *Molecular Probes Handbook* by Richard P. Hoagland.

A secondary label can be used in a method of the present disclosure. A secondary label is a binding moiety that can bind specifically to a partner moiety. For example, a ligand moiety can be attached to a polymerase, nucleic acid or nucleotide to allow detection via specific affinity for labeled receptor. Exemplary pairs of binding moieties that can be used include, without limitation, antigen and immunoglobulin or active fragments thereof, such as FAbs; immunoglobulin and immunoglobulin (or active fragments, respectively); avidin and biotin, or analogs thereof having specificity for avidin; streptavidin and biotin, or analogs thereof having specificity for streptavidin; or carbohydrates and lectins.

In some embodiments, the secondary label can be a chemically modifiable moiety. In this embodiment, labels having reactive functional groups can be incorporated into a stabilized ternary complex. Subsequently, the functional group can be covalently reacted with a primary label moiety. Suitable functional groups include, but are not limited to, amino groups, carboxy groups, maleimide groups, oxo groups, groups that participate in click reactions and thiol groups.

A label can be attached to a nucleotide, polymerase or other molecule via a linker. A linker that is present in a nucleotide or polymerase can be, but need not be, cleavable. For example, the linker can be stable to conditions used in methods set forth herein such that the covalent structure of the linker is not changed during any particular step, or throughout all steps, of a method set forth herein. A linker that is present in a nucleotide analog can be at least as chemically stable as one or more other moieties in the analog. For example, the linker can be as chemically stable as the nitrogenous base, sugar and/or phosphate moiety during any particular step, or throughout all steps, of a method set forth herein.

In alternative embodiments, a ternary complex can lack exogenous labels. For example, a stabilized ternary complex and all components participating in the stabilized ternary complex (e.g. polymerase, template nucleic acid, primer and/or cognate nucleotide) can lack one, several or all of the exogenous labels described herein or in the references that are cited and incorporated herein. In such embodiments, ternary complexes can be detected based on intrinsic properties of the stabilized ternary complex, such as mass, charge, intrinsic optical properties or the like. Exemplary methods for detecting non-labeled ternary complexes are set forth in commonly owned U.S. Pat. App. Pub. No. 2017/0022553 A1 PCT App. Ser. No. PCT/US16/68916 (published as WO 2017/117243 A1), or U.S. Pat. App. Ser. Nos. 62/375,379 (now published as US Pat. App. Pub. No. 2018/0044727 A1 or Ser. No. 15/677,870, published as US Pat. App. Pub. No. 2018/0044715 A1, each of which is incorporated herein by reference.

Generally, detection can be achieved in an examination step by methods that perceive a property that is intrinsic to a ternary complex or a label moiety attached thereto. Exemplary properties upon which detection can be based include, but are not limited to, mass, electrical conductivity, energy absorbance, luminescence (e.g. fluorescence) or the like. Detection of luminescence can be carried out using methods known in the art pertaining to nucleic acid arrays. A luminophore can be detected based on any of a variety of luminescence properties including, for example, emission wavelength, excitation wavelength, fluorescence resonance energy transfer (FRET) intensity, quenching, anisotropy or lifetime. Other detection techniques that can be used in a method set forth herein include, for example, mass spectrometry which can be used to perceive mass; surface plasmon resonance which can be used to perceive binding to a surface; absorbance which can be used to perceive the wavelength of the energy a label absorbs; calorimetry which can be used to perceive changes in temperature due to presence of a label; electrical conductance or impedance which can be used to perceive electrical properties of a label, or other known analytic techniques. Examples of reagents and conditions that can be used to create, manipulate and detect stabilized ternary complexes include, for example, those set forth in commonly owned U.S. Pat. App. Pub. No. 2017/0022553 A1; PCT App. Ser. No. PCT/US16/68916, published as WO 2017/117243 A1; or U.S. patent application Ser. No. 15/677,870, published as US Pat. App. Pub. No. 2018/0044715 A1; Ser. No. 15/851,383, published as US Pat. App. Pub. No. 2018/0187245 A1; Ser. No. 15/873,343, published as US Pat. App. Pub. No. 2018/0208983 A1; US Pat. App. Pub. No. 2018/0208983 A1, which claims priority to 62/450,397 and 62/506,759, each of which is incorporated herein by reference.

Detection of ternary complexes can take place in different types of reaction mixtures, but generally takes place under conditions that stabilize ternary complexes. The conditions can also be selected to reduce the concentration of labeled species (e.g., labeled nucleotides) below the level that was used to form the ternary complex. Optionally, an examination step, or sub-step, involves detecting the interaction of a polymerase and cognate nucleotide with a primed template nucleic acid in the absence of non-complexed labeled nucleotide and polymerase. Optionally, the examination step or sub-step involves detecting a labeled nucleotide in a stabilized ternary complex after non-bound nucleotides have been removed from contact with the ternary complex using a stabilizing fluid. The formation of a ternary complex may be detected or monitored by detecting or monitoring a label attached to the nucleotide that participates in the ternary complex. Optionally, the absence of formation of ternary complex is detected or monitored. Optionally, the dissociation of a ternary complex is monitored.

A step for detecting ternary complexes can take place during a wash step carried out using a ternary complex stabilizing fluid. The stabilizing fluid can contain $Li^+$, PEI, betaine or an inhibitory metal cation (e.g. $Ca^{2+}$). Optionally, the stabilizing fluid is held static (i.e., not moving or flowing) during the detection step. However, the fluid can flow, for example, through a flow cell that contains a ternary complex that is to be detected. Advantageously, detection of ternary complexes during a wash step can reduce background signal associated with non-bound nucleotides or polymerases that may harbor detectable labels. Again, by this approach ternary complex detection can take place in a reaction mixture different from the reaction mixture that provided the labeled nucleotide(s) to the primed template nucleic acid molecule, which optionally can be blocked at its 3'-end with a reversible terminator moiety.

Examination and detection of a stabilized ternary complex may be accomplished in different ways. For example, monitoring can include measuring association kinetics for the interaction between two or more of the components of the complex. Monitoring the interaction can include measuring equilibrium binding signals or equilibrium binding constants. Thus, for example, the monitoring may include measuring equilibrium binding signals, or the equilibrium binding constant in the presence of one or more of the labeled nucleotides. Monitoring the interaction can include, for example, measuring dissociation kinetics of the nucleotide from the primed template nucleic acid in the presence of any one of the four nucleotides. Optionally, monitoring the interaction of the polymerase with the primed template nucleic acid molecule in the presence of a nucleotide molecule includes measuring the kinetics of the dissociation of the closed complex. Techniques for measuring association, equilibrium and dissociation kinetics are known and can be readily modified for use in a method set forth herein by one in the art. See, for example, Markiewicz et al., *Nucleic Acids Research* 40(16):7975-84 (2012); Xia et al., *J. Am. Chem. Soc.* 135(1):193-202 (2013); Brown et al., *J. Nucleic Acids*, Article ID 871939, 11 pages (2010); Washington, et al., *Mol. Cell. Biol.* 24(2):936-43 (2004); Walsh and Beuning, *J. Nucleic Acids*, Article ID 530963, 17 pages (2012); and Roettger, et al., *Biochemistry* 47(37):9718-9727 (2008), which are incorporated by reference herein. It will be understood that a detection technique can accumulate signal over a relatively brief duration as is typically understood to be a single timepoint acquisition. Alternatively, signal can be continuously monitored over time as is typical of a time-based acquisition. It is also possible to acquire a series of timepoints in a periodic fashion to obtain a time-based acquisition.

Some embodiments of the methods set forth herein utilize two or more distinguishable signals to distinguish stabilized ternary complexes from each other and/or to distinguish one base type in a template nucleic acid from another base type. For example, two or more luminophores can be distinguished from each other based on unique optical properties such as unique wavelength for excitation or unique wavelength of emission. In particular embodiments, a method can distinguish different stabilized ternary complexes based on differences in luminescence intensity. For example, a first ternary complex can be detected in a condition where it emits less intensity than a second ternary complex. Such intensity scaling (sometimes called 'grey scaling') can exploit any distinguishable intensity difference. Exemplary differences include a particular stabilized ternary complex having an intensity that is 10%, 25%, 33%, 50%, 66%, or 75% compared to the intensity of another stabilized ternary complex that is to be detected.

Intensity differences can result from use of different luminophores each having a different extinction coefficient (i.e. resulting in different excitation properties) and/or different luminescence quantum yield (i.e. resulting in different emission properties). Alternatively, the same luminophore type can be used but can be present in different amounts. For example, all members of a first population of ternary complexes can be labeled with a particular luminophore, whereas a second population has only half of its members labeled with the luminophore. In this example, the second population would be expected to produce half the signal of the first population. The second population can be produced, for example, by using a mixture of labeled nucleotides and unlabeled nucleotides (in contrast to the first population containing primarily labeled nucleotides). Similarly, the second population can be produced, for example, by using a mixture of labeled polymerases and unlabeled polymerases (in contrast to the first population containing primarily labeled polymerases). In an alternative labeling scheme, a first population of ternary complexes can include polymerase molecules that have multiple labels that produce a particular luminescent signal and a second population of ternary complexes can include polymerase molecules that each have only one of the labels that produces the luminescent signal.

In some embodiments, the examination step is carried out in a way that the identity of at least one nucleotide type is imputed, for example, as set forth in commonly owned U.S. Pat. No. 9,951,385 or U.S. patent application Ser. No. 15/922,787, published as US Pat. App. Pub. No. 2018/0305749 A1, each of which is incorporated herein by reference. For example, an examination step can include steps of (a) providing a fluid that includes a primed template nucleic acid, a polymerase and nucleotide cognates of first, second and third base types in the template under ternary complex stabilizing conditions; (b) optionally removing non-bound polymerase and non-bound nucleotides from the fluid; (c) examining the fluid to determine whether a ternary complex formed, wherein the fluid includes $Li^+$, PEI, betaine and/or an inhibitory metal cation (e.g. $Ca^{2+}$); and (d) identifying the next correct nucleotide for the primed template nucleic acid molecule, wherein the next correct nucleotide is identified as a cognate of the first, second or third base type if ternary complex is detected in step (c), and wherein the next correct nucleotide is imputed to be a nucleotide cognate of a fourth base type based on the absence of a ternary complex in step (c).

Alternatively or additionally to using imputation, an examination step can use a decoding or disambiguation scheme to identify one or more nucleotide types, for example, as set forth in commonly owned U.S. Pat. No. 9,951,385 or U.S. patent application Ser. No. 15/922,787, published as US Pat. App. Pub. No. 2018/0305749 A1, each of which is incorporated herein by reference. For example, examination can be carried out by (a) contacting a primed template nucleic acid with a polymerase and a first mixture of nucleotides under ternary complex stabilizing conditions, wherein the first mixture includes a nucleotide cognate of a first base type and a nucleotide cognate of a second base type; (b) contacting the primed template nucleic acid with a polymerase and a second mixture of nucleotides under ternary complex stabilizing conditions, wherein the second mixture includes a nucleotide cognate of the first base type and a nucleotide cognate of a third base type; (c) examining products of steps (a) and (b) for signals produced by a ternary complex that includes the primed template nucleic acid, a polymerase and a next correct nucleotide, wherein signals acquired for the product of step (a) are ambiguous for the first and second base type, and wherein signals acquired for the product of step (b) are ambiguous for the first and third base type, wherein the products of steps (a) and (b) are examined in the presence of $Li^+$, PEI, betaine and/or an inhibitory metal cation (e.g. $Ca^{2+}$); (d) disambiguating signals acquired in step (c) to identify a base type that binds the next correct nucleotide. Optionally, to achieve disambiguation (i) the first base type is correlated with presence of signals for the product of step (a) and presence of signals for the product of step (b), (ii) the second base type is correlated with presence of signals for the product of step (a) and absence of signals for the product of step (b), and (iii) the third base type is correlated with absence of signals for the product of step (a) and presence of signals for the product of step (b). Optionally, non-bound polymerase and/or non-bound nucleotide are removed from the products of steps (a) and (b) prior to step (c).

The disclosed techniques provide advantages over a variety of other techniques used in the DNA sequencing field. For example, there is no requirement for a label (e.g., a FRET partner) to be present on a polymerase or primed template nucleic acid. Indeed, in certain embodiments the polymerase is unlabeled, or does not generate any signal used for identifying cognate or non-cognate nucleotide in a ternary complex. Signal energy (e.g. FRET) need not transfer between a polymerase and a labeled nucleotide to render the ternary complex detectable in a method of the present disclosure. A label or dye of a detectable nucleotides employed in a method herein need not be an intercalating dye (e.g., not an intercalating dye disclosed in U.S. Pat. No. 8,399,196), that changes its signal-generating properties (e.g., fluorescent output) upon participating in a ternary complex. As well, the label or dye present on a labeled nucleotide need not be a conformationally sensitive dye that changes spectral properties when it is the cognate nucleotide present in a ternary complex.

In some embodiments, a method of the present disclosure can include a step of extending a primer. For example, a method of detecting a primed template nucleic acid can include the steps of: (a) providing a mixture that includes a ternary complex, the ternary complex including a primed template nucleic acid, a polymerase, and a nucleotide cognate for the next base of the primed template nucleic acid, wherein the mixture further includes excess polymerase of the same type present in the ternary complex and excess nucleotide of the same type present in the ternary complex; (b) replacing the excess polymerase and the excess nucleotide with a fluid containing $Li^+$, PEI, betaine and/or an inhibitory metal cation (e.g. $Ca^{2+}$); (c) detecting the ternary complex while it is in contact with the fluid containing the stabilizing agent; (d) identifying the next correct base for the primed template nucleic acid molecule from the result of step (c); and (e) extending the primer of primed template nucleic acid. Optionally, the method can further include a step of (f) repeating steps (a) through (e) using the primed template nucleic acid having the extended primer in place of the primed template nucleic acid.

In yet another example of a method that includes a primer extension step, the steps of the method can include: (a) providing a mixture that includes a ternary complex, the ternary complex including a primed template nucleic acid, a polymerase, and a nucleotide cognate for the next base of the primed template nucleic acid, wherein the mixture further includes excess nucleotide of the same type present in the ternary complex; (b) replacing the excess nucleotide with a fluid containing $Li^+$, PEI, betaine and/or an inhibitory metal cation (e.g. $Ca^{2+}$) (c) detecting the ternary complex while it is in contact with the fluid containing $Li^+$, PEI, betaine and/or an inhibitory metal cation (e.g. $Ca^{2+}$) (d) identifying the next correct base for the primed template nucleic acid molecule from the result of step (c); and (e) extending the primer of primed template nucleic acid. Optionally, the method can further include a step of (f) repeating steps (a) through (e) using the primed template nucleic acid having the extended primer in place of the primed template nucleic acid.

A primer extension step can be carried out by contacting a primed template nucleic acid with an extension reaction mixture. Typically, fluid that was present in a previous examination step is removed and replaced with the extension reaction mixture. Alternatively, the extension reaction mixture can be formed by adding one or more reagents to the fluid that was present in the examination step. Optionally, the extension reaction mixture includes a different composition of nucleotides than an examination step. For example, an examination step can include one or more nucleotide types that are not present in the extension reaction and vice versa. By way of more specific example, an extension step can omit at least one type of nucleotide and an examination step can employ at least four types of nucleotides. Optionally, one or more nucleotide types is added to an examination mixture for a primer extension step.

Nucleotides present in an examination step may cause unwanted nucleotide incorporation if carried over into an extension step. Thus, a wash step can be employed prior to a primer extension step to remove nucleotides. Optionally, free nucleotides may be removed by enzymes such as phosphatases, by chemical modification or by physical separation techniques.

A primer extension step can use any of a variety of polymerases including, for example, a polymerase set forth above in the context of forming a ternary complex. However, the polymerase used for extension will be catalytically active and used in a condition that does not preclude catalysis. A polymerase that is used for an extension step need not be attached to an exogenous label (e.g. covalently or otherwise). Alternatively, a polymerase that is used for primer extension can include an exogenous label, for example, a label that was used in a previous examination step. Ternary complex formation and extension steps can use the same type of polymerase, albeit in different conditions. Alternatively, the two steps can be carried out by different types of polymerases.

Adding a reversibly terminated nucleotide to the 3' end of a primer provides a means to prevent more than one nucleotide from being added to the primer during the extension step and further prevents unwanted extension of the primer in a subsequent examination step. Thus, a position in a template that is adjacent to a nucleotide of a particular type can be examined. In such embodiments, a stabilized ternary complex can be formed at the position and examined to detect the next correct nucleotide for the template that is hybridized to the extended, reversibly terminated primer. The method can be repeated in a step-wise fashion by then removing or modifying the reversible terminator moiety from the extended, reversibly terminated primer to produce an extendible primer.

Typically, a reversibly terminated nucleotide that is added to a primer in a method set forth herein does not have an exogenous label. This is because the extended primer need not be detected in a method set forth herein. However, if desired, one or more types of reversibly terminated nucleotides used in a method set forth herein can be detected, for example, via exogenous labels attached to the nucleotides. Exemplary reversible terminator moieties, methods for incorporating them into primers and methods for modifying the primers for further extension (often referred to as 'deblocking') are set forth in U.S. Pat. Nos. 7,544,794; 7,956,171; 8,034,923; 8,071,755; 8,808,989; or 9,399,798. Further examples are set forth in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference. Further examples of reagents and conditions that can be used for a polymerase-based primer extension step include, for example, those set forth in commonly owned U.S. Pat. App. Pub. No. 2017/0022553 A1 or U.S. patent application Ser. No. 15/677,870, published as US Pat. App. Pub. No. 2018/0044727 A1; Ser. No. 15/581,383, published as US Pat. App. Pub. No. 2018/0208922 A1; or US Pat. App. Pub. No. 2018/0208983 A1, which claims priority to 62/450,397 and 62/506,759, each of which is incorporated herein by reference.

A method of the present disclosure can include a step of contacting a primed template nucleic acid with a polymerase and a mixture of nucleotides under conditions to produce an extended primer hybrid. One or more of the nucleotides in the mixture can be reversibly terminated. For example, at least 1, 2, 3, 4 or more nucleotide types in the mixture can be reversibly terminated. Alternatively or additionally, at most 4, 3, 2, or 1 nucleotide types in the mixture can be reversibly terminated. Similarly, one or more nucleotide types that are reversibly terminated in the mixture can be complementary to at least 1, 2, 3 or 4 base types in a template nucleic acid. Alternatively or additionally, the reversibly terminated nucleotide types in the mixture can be complementary to at most 4, 3, 2, or 1 base types in a template nucleic acid. Reversibly terminated and non-terminated nucleotides can be present simultaneously in an extension reaction. For example, some or all of the nucleotide types can be delivered simultaneously in a single extension reaction. Alternatively, different nucleotide types can be serially delivered (individually or in subsets) such that they are combined into a single extension reaction. Use of a mixture of terminated and extendible nucleotides can allow for determination of a low-resolution sequence and/or to extend read lengths as set forth, for example, in U.S. patent application Ser. No. 16/265,942, which claims priority to U.S. App. Ser. No. 62/626,836, each of which is incorporated herein by reference.

In particular embodiments, reagents that are used during a primer extension step are removed from contact with the primed template nucleic acid prior to a step of forming a stabilized ternary complex with the primed template nucleic acid. For example, removal of a nucleotide mixture that was used for an extension step can be desirable when one or more types of nucleotides in the mixture would interfere with formation or detection of a ternary complex in a subsequent examination step. Similarly, it may be desirable to remove polymerases or cofactors that were used in a primer extension step to prevent unwanted catalytic activity during the examination step. Removal can be followed by a wash step, wherein an inert fluid is used to purge the primed template nucleic acid of residual components of the extension mixture.

Wash steps can be performed between any of a variety of steps set forth herein. For example, a wash step can be useful for separating a primed template nucleic acid from other reagents that were contacted with the primed template nucleic acid under ternary complex stabilizing conditions. Such a wash can remove one or more reagents from interfering with examination of a mixture or from contaminating a second mixture that is to be formed on a substrate (or in a vessel) that had previously been in contact with the first mixture. For example, a primed template nucleic acid can be contacted with a polymerase and at least one nucleotide type to form a first mixture under ternary complex stabilizing conditions, and the first mixture can be examined. Optionally, a wash can be carried out prior to examination to remove reagents that are not participating in formation of a stabilized ternary complex. Alternatively or additionally, a wash can be carried out after the examination step to remove one or more component of the first mixture from the primed template nucleic acid. Then the primed template nucleic acid can be contacted with a polymerase and at least one other nucleotide to form a second mixture under ternary complex stabilizing conditions, and the second mixture can be examined for ternary complex formation. As before, an optional wash can be carried out prior to the second examination to remove reagents that are not participating in formation of a stabilized ternary complex. Washes that are contacted with a ternary complex can include a stabilizing fluid such as those that include $Li^+$, PEI, betaine, inhibitory metal ion (e.g. $Ca^{2+}$) or other ternary complex stabilizing agents set forth herein.

A method of the present disclosure can include multiple repetitions of steps set forth herein. Such repetition can provide a sequence for a template nucleic acid or a signature for the template nucleic acid. Examination and extension steps can be repeated multiple times as can optional steps of deblocking primers or washing away unwanted reactants or products between various steps. Accordingly, a primed template nucleic acid can be subjected at least 2, 5, 10, 25, 50, 100 or more steps of a method set forth herein. Not all of the steps need to be repeated nor do repeated steps need to occur in the same order in each repetition. For example, next correct nucleotides at each position of a template can be identified using real time analysis (i.e. in parallel with fluidic and detection steps of a sequencing method). However, real time analysis is not necessary and instead next correct nucleotides can be identified after some or all of the fluidic and detection steps have been completed.

A stabilized ternary complex, or a component that is capable of forming (i.e. participating in the formation of) a stabilized ternary complex, can be attached to a solid support. The solid support can be made from any of a variety of materials used for analytical biochemistry. Suitable materials may include glass, polymeric materials, silicon, quartz (fused silica), borofloat glass, silica, silica-based materials, carbon, metals, an optical fiber or bundle of optical fibers, sapphire, or plastic materials. The particular material can be selected based on properties desired for a particular use. For example, materials that are transparent to a desired wavelength of radiation are useful for analytical techniques that will utilize radiation of that wavelength. Conversely, it may be desirable to select a material that does not pass radiation of a certain wavelength (e.g. being opaque, absorptive or reflective). Other properties of a material that can be exploited are inertness or reactivity to certain reagents used in a downstream process, such as those set forth herein, or ease of manipulation, or low cost of manufacture.

A particularly useful solid support is a particle such as a bead or microsphere. Populations of beads can be used for attachment of populations of stabilized ternary complexes or components capable of forming the complexes (e.g. polymerases, templates, primers or nucleotides). In some embodiments, it may be useful to use a configuration whereby each bead has a single type of stabilized ternary complex or a single type of component capable of forming the complex. For example, an individual bead can be attached to a single type of ternary complex, a single type of template allele, a single type of template locus, a single type of allele-specific primer, a single type of locus-specific primer or a single type of nucleotide. Alternatively, different types of components need not be separated on a bead-by-bead basis. As such, a single bead can bear multiple different types of ternary complexes, template nucleic acids, primers, primed template nucleic acids and/or nucleotides. The composition of a bead can vary, depending for example, on the format, chemistry and/or method of attachment to be used. Exemplary bead compositions include solid supports, and chemical functionalities imparted thereto, used in protein and nucleic acid capture methods. Such compositions include, for example, plastics, ceramics, glass, polystyrene, melamine, methylstyrene, acrylic polymers, paramagnetic materials, thoria sol, carbon graphite, titanium dioxide, latex or cross-linked dextrans such as Sepharose™, cellulose, nylon, cross-linked micelles and Teflon™, as well as other materials set forth in "Microsphere Detection Guide" from Bangs Laboratories, Fishers Ind., which is incorporated herein by reference.

The geometry of a particle, bead or microsphere also can correspond to a wide variety of different forms and shapes. For example, they can be symmetrically shaped (e.g. spherical or cylindrical) or irregularly shaped (e.g. controlled pore glass). In addition, beads can be porous, thus increasing the surface area available for capture of ternary complexes or components thereof. Exemplary sizes for beads used herein can range from nanometers to millimeters or from about 10 nm-1 mm.

In particular embodiments, beads can be arrayed or otherwise spatially distinguished. Exemplary bead-based arrays that can be used include, without limitation, a BeadChip™ Array available from Illumina, Inc. (San Diego, Calif.) or arrays such as those described in U.S. Pat. Nos. 6,266,459; 6,355,431; 6,770,441; 6,859,570; or 7,622,294; or PCT Publication No. WO 00/63437, each of which is incorporated herein by reference. Beads can be located at discrete locations, such as wells, on a solid-phase support, whereby each location accommodates a single bead. Alternatively, discrete locations where beads reside can each include a plurality of beads as described, for example, in U.S. Pat. App. Pub. Nos. 2004/0263923 A1, 2004/0233485 A1, 2004/0132205 A1, or 2004/0125424 A1, each of which is incorporated herein by reference.

As will be recognized from the above bead array embodiments, a method of the present disclosure can be carried out in a multiplex format whereby multiple different types of nucleic acids are detected in parallel in a method set forth herein. Although it is also possible to serially process different types of nucleic acids using one or more steps of the methods set forth herein, parallel processing can provide cost savings, time savings and uniformity of conditions. A composition or method of the present disclosure can include at least 2, 10, 100, $1\times10^3$, $1\times10^4$, $1\times10^5$, $1\times10^6$, $1\times10^9$, or more different nucleic acids. Alternatively or additionally, a composition or method of the present disclosure can include at most $1\times10^9$, $1\times10^6$, $1\times10^5$, $1\times10^4$, $1\times10^3$, 100, 10, 2 or fewer, different nucleic acids. Accordingly, various reagents or products set forth herein as being useful in the apparatus or methods (e.g. primed template nucleic acid or stabilized ternary complexes) can be multiplexed to have different types or species in these ranges.

Further examples of commercially available arrays that can be used include, for example, an Affymetrix GeneChip™ array. A spotted array can also be used according to some embodiments. An exemplary spotted array is a CodeLink™ Array available from Amersham Biosciences. Another array that is useful is one that is manufactured using inkjet printing methods such as SurePrint™ Technology available from Agilent Technologies.

Other useful arrays include those that are used in nucleic acid sequencing applications. For example, arrays that are used to immobilize amplicons of genomic fragments (often referred to as clusters) can be particularly useful. Examples of nucleic acid sequencing arrays that can be used herein include those described in Bentley et al., Nature 456:53-59 (2008), PCT Pub. Nos. WO 91/06678; WO 04/018497 or WO 07/123744; U.S. Pat. Nos. 7,057,026; 7,211,414; 7,315,019; 7,329,492 or 7,405,281; or U.S. Pat. App. Pub. No. 2008/0108082, each of which is incorporated herein by reference.

A nucleic acid can be attached to a support in a way that provides detection at a single molecule level or at an ensemble level. For example, a plurality of different nucleic acids can be attached to a solid support in a way that an individual stabilized ternary complex that forms on one nucleic acid molecule on the support can be distinguished from all neighboring ternary complexes that form on the nucleic acid molecules of the support. As such, one or more different templates can be attached to a solid support in a format where each single molecule template is physically isolated and detected in a way that the single molecule is resolved from all other molecules on the solid support.

Alternatively, a method of the present disclosure can be carried out for one or more nucleic acid ensembles, an ensemble being a population of nucleotides having a common template sequence. Cluster methods can be used to attach one or more ensembles to a solid support. As such, an array can have a plurality of ensembles, each of the ensembles being referred to as a cluster or array feature in that format. Clusters can be formed using methods known in the art such as bridge amplification or emulsion PCR. Useful bridge amplification methods are described, for example, in U.S. Pat. Nos. 5,641,658 or 7,115,400; or U.S. Patent Pub. Nos. 2002/0055100 A1; 2004/0002090 A1; 2004/0096853 A1; 2007/0128624 A1; or 2008/0009420 A1. Emulsion PCR methods include, for example, methods described in Dressman et al., Proc. Natl. Acad. Sci. USA 100:8817-8822 (2003), WO 05/010145, or U.S. Patent Pub. Nos. 2005/0130173 A1 or 2005/0064460 A1, each of which is incorporated herein by reference in its entirety. Another useful method for amplifying nucleic acids on a surface to form clusters is rolling circle amplification (RCA), for example, as described in Lizardi et al., Nat. Genet. 19:225-232 (1998) or US 2007/0099208 A1, each of which is incorporated herein by reference.

In particular embodiments, a stabilized ternary complex, polymerase, nucleic acid or nucleotide is attached to a flow cell surface or to a solid support in a flow cell. A flow cell allows convenient fluidic manipulation by passing solutions into and out of a fluidic chamber that contacts the support-bound, ternary complex. The flow cell also provides for detection of the fluidically manipulated components. For example, a detector can be positioned to detect signals from the solid support, such as signals from a label that is recruited to the solid support due to formation of a stabilized ternary complex. Exemplary flow cells that can be used are described, for example, in US Pat. App. Pub. No. 2010/0111768 A1, WO 05/065814 or US Pat. App. Pub. No. 2012/0270305 A1, each of which is incorporated herein by reference.

The present disclosure provides systems for detecting nucleic acids, for example, using methods set forth herein. For example, a system can be configured for reactions involving the examination of the interaction between a polymerase and a primed template nucleic acid in the presence of nucleotides to identify one or more bases in a template nucleic acid sequence. Optionally, a system includes components and reagents for performing one or more steps set forth herein including, but not limited to, forming at least one stabilized ternary complex between a primed template nucleic acid, polymerase and next correct nucleotide; contacting a ternary complex with stabilizing fluid; detecting the stabilized ternary complex(es); extending the primer of each primed template nucleic acid; and/or identifying a nucleotide, sequence of nucleotides, or series of base multiplets present in the template.

A system of the present disclosure can include a vessel or solid support for carrying out a nucleic acid detection method. For example, the system can include an array, flow cell, multi-well plate or other convenient apparatus. The vessel or solid support can be removable, thereby allowing it to be placed into or removed from the system. As such, a system can be configured to sequentially process a plurality of vessels or solid supports. The system can include a fluidic system having reservoirs for containing one or more of the reagents set forth herein (e.g. polymerase, primer, template nucleic acid, nucleotide(s) for ternary complex formation, nucleotides for primer extension, deblocking reagents, stabilizing fluid or mixtures of such components). The fluidic system can be configured to deliver reagents to a vessel or solid support, for example, via channels or droplet transfer apparatus (e.g. electrowetting apparatus). Any of a variety of detection apparatus can be configured to detect the vessel or solid support where reagents interact. Examples include luminescence detectors, surface plasmon resonance detectors and others known in the art. Exemplary systems having fluidic and detection components that can be readily modified for use in a system herein include, but are not limited to, those set forth in U.S. Pat. App. Ser. No. 62/481,289 or Ser. No. 15/922,661, published as US Pat. App. Pub. No. 2018/0280975 A1; U.S. Pat. Nos. 8,241,573; 7,329,860 or 8,039,817; or US Pat. App. Pub. Nos. 2009/0272914 A1 or 2012/0270305 A1, each of which is incorporated herein by reference.

Optionally, a system of the present disclosure further includes a computer processing unit (CPU) that is configured to operate system components. The same or different CPU can interact with the system to acquire, store and process signals (e.g. signals detected in a method set forth herein). In particular embodiments, a CPU can be used to determine, from the signals, the identity of the nucleotide that is present at a particular location in a template nucleic acid. In some cases, the CPU will identify a sequence of nucleotides for the template from the signals that are detected.

A useful CPU can include one or more of a personal computer system, server computer system, thin client, thick client, hand-held or laptop device, multiprocessor system, microprocessor-based system, set top box, programmable consumer electronic, network PC, minicomputer system, mainframe computer system, smart phone, and distributed cloud computing environments that include any of the above systems or devices, and the like. The CPU can include one or more processors or processing units, a memory architecture that may include RAM and non-volatile memory. The memory architecture may further include removable/non-removable, volatile/non-volatile computer system storage media. Further, the memory architecture may include one or more readers for reading from and writing to a non-removable, non-volatile magnetic media, such as a hard drive, a magnetic disk drive for reading from and writing to a removable, non-volatile magnetic disk, and/or an optical disk drive for reading from or writing to a removable, non-volatile optical disk such as a CD-ROM or DVD-ROM. The CPU may also include a variety of computer system readable media. Such media may be any available media that is accessible by a cloud computing environment, such as volatile and non-volatile media, and removable and non-removable media.

The memory architecture may include at least one program product having at least one program module implemented as executable instructions that are configured to carry out one or more steps of a method set forth herein. For example, executable instructions may include an operating system, one or more application programs, other program modules, and program data. Generally, program modules may include routines, programs, objects, components, logic, data structures, and so on, that perform particular tasks set forth herein.

The components of a CPU may be coupled by an internal bus that may be implemented as one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

A CPU can optionally communicate with one or more external devices such as a keyboard, a pointing device (e.g. a mouse), a display, such as a graphical user interface (GUI), or other device that facilitates interaction of a use with the nucleic acid detection system. Similarly, the CPU can communicate with other devices (e.g., via network card, modem, etc.). Such communication can occur via I/O interfaces. Still yet, a CPU of a system herein may communicate with one or more networks such as a local area network (LAN), a general wide area network (WAN), and/or a public network (e.g., the Internet) via a suitable network adapter.

The present disclosure further provides a composition of matter that includes one or more of the components set forth herein, for example, in the context of methods for stabilizing a ternary complex. In particular embodiments, the composition includes a fluid, the fluid containing a ternary complex and $Li^+$, wherein the ternary complex includes a primed template nucleic acid, a polymerase, and a nucleotide cognate for the next correct base for the primed template nucleic acid molecule. The fluid can further contain one or more of betaine, PEI or an inhibitory metal ion (e.g. $Ca^{2+}$). Optionally, the ternary complex is immobilized on a solid support, for example, via attachment of the template nucleic acid to the solid support. The material for the solid support and attachment means can be any of a variety of those set forth herein or known in the art. For example, the solid support can include an array of features and each feature can include an immobilized ternary complex. The features can have a size, spacing, density or other characteristic in accordance with the disclosure set forth previously herein. One or more components of the ternary complex, for example, the polymerase and/or nucleotide, can contain an exogenous label such as a luminophore or another label set forth herein. The fluid can further include non-bound nucleotide cognates for at least 1, 2, 3, or 4 bases suspected of being in the template nucleic acid. The non-bound nucleotide cognates can have different exogenous labels that distinguish one nucleotide type from another. Alternatively or additionally, the fluid can include non-bound polymerase that optionally contains an exogenous label. In particular embodiments, the primed template nucleic acid includes a blocked primer (e.g. a reversibly terminated primer). The concentration of ternary complex in the fluid can be greater than the concentration of non-bound nucleotide and/or greater than the concentration of non-bound polymerase in the fluid. The fluid can be an aqueous fluid. The fluid can lack alcohol, oil or other solvents that do not dissolve nucleotides or polymerases including, for example, the non-miscible fluids set forth in U.S. patent application Ser. No. 16/164,417, which claims priority to U.S. Pat. App. Ser. No 62/574,308, each of which is incorporated herein by reference.

This disclosure further provides kits that can be used, for example, for characterizing nucleic acids. A kit can include reagents for carrying out one or more of the methods set forth herein. For example, a kit can include reagents for producing a stabilized ternary complex when mixed with one or more primed template nucleic acid. More specifically, a kit can include one or more of $Li^+$, PEI, betaine or an inhibitory metal ion (e.g. $Ca^{2+}$) used in a method set forth herein, including for example, the methods set forth in the Examples section below. In addition, the kit can include at least one nucleotide type and a polymerase that is capable of forming a stabilized ternary complex. A polymerase that is used for an extension step can also be included in a kit. The nucleotides, polymerase or both can include an exogenous label, for example, as set forth herein in the context of various methods.

Accordingly, any of the components or articles used in performing the methods set forth herein can be usefully packaged into a kit. For example, the kits can be packed to include some, many or all of the components or articles used in performing the methods set forth herein. Exemplary components include, for example, labeled nucleotides (e.g. extendible labeled nucleotides); polymerases (labeled or unlabeled); nucleotides having terminator moieties (e.g. unlabeled, reversibly terminated nucleotides); stabilizing fluids such as those containing $Li^+$, PEI, betaine and/or an inhibitory metal cation (e.g. $Ca^{2+}$); deblocking reagents and the like as set forth herein and in references cited herein. Any of such reagents can include, for example, some, many or all of the fluids, components and/or articles used for performing one or more of the subsequent steps for analysis of a primed template nucleic acid. A kit need not include a primer or template nucleic acid. Rather, a user of the kit can provide a primed template nucleic acid which is to be combined with components of the kit. Similarly, a kit can exclude one or more of the components set forth herein and, optionally, such excluded components can be provided by an end user.

One or more ancillary reagents also can be included in a kit. Such ancillary reagents can include any of the reagents exemplified above and/or other types of reagents useful in performing the methods set forth herein. Instructions can further be included in a kit. The instructions can include, for example, procedures for making any components used in the methods set forth herein, performing one or more steps of any embodiment of the methods set forth herein and/or instructions for performing any of the subsequent analysis steps employing a primed template nucleic acid.

In particular embodiments, a kit includes a cartridge having reservoirs to contain the reagents and further having fluidic components for transferring reagents from the reservoirs to a detection instrument. For example, the fluidic components can be configured to transfer reagents to a flow cell where stabilized ternary complexes are detected. An exemplary fluidic cartridge that can be included in a kit (or system) of the present disclosure is described in U.S. patent application Ser. No. 15/922,661, published as US Pat. App. Pub. No. 2018/0280975 A1, claiming priority to 62/481,289, each of which is incorporated herein by reference.

EXAMPLE I

Stabilizing Ternary Complexes with an Aqueous Stabilizing Fluid that Solubilizes Polymerase and Nucleotide This example demonstrates examination of a blocked primed template nucleic acid in a manner that assessed binding of each of four different labeled nucleotides individually. An aqueous solution containing an agent that was capable of stabilizing ternary complexes was used to: (1) deliver examination solutions containing polymerase, labeled nucleotide, and magnesium cations; (2) separate immobilized ternary complexes from contact with non-bound polymerase and labeled nucleotide; and (3) facilitate ternary complex detection over an extended period during an imaging wash step. Different nucleotides used in the procedure were labeled with the same type of fluorescent detectable label and each type of nucleotide was separately delivered and examined. Alternatively, the nucleotides could have had different detectable labels, respectively, and several different labeled nucleotide types could have been contacted with the blocked primed template nucleic acid at the same time.

Flow cells containing primed template nucleic acids were prepared as follows. Template nucleic acid strands synthesized in 12 PCR reactions using 5'-biotinylated primers were prepared, and then independently bound to streptavidin-coated magnetic beads. This resulted in a population of 12 bead types, where each bead harbored a homogenous collection of template strands. Beads used in the procedure had been functionalized with 1 mM NHS-PEG4-TCO in phosphate buffered saline (PBS). Beads harboring immobilized template strands were next flowed over an aminosilane flow cell surface that had been functionalized with tetrazine. The mixture was incubated for one hour to permit covalent attachment of the decorated beads to the functionalized surface within the flow cell.

Next, sequencing primers were flowed into the flow cell and allowed to hybridize to the immobilized template strands. Among the aggregated collection of beads, there were primed template nucleic acids having each of the four bases (i.e., A, C, G or T) as the next template nucleotide. Reversible terminator nucleotides were then incorporated at the 3'-ends of the hybridized sequencing primers to create a collection of blocked primed template nucleic acid molecules. This was accomplished using a pH-buffered incorporation mixture that included 10 U/ml Therminator™ polymerase, and 200 nM of unlabeled reversibly terminated nucleotide analogs of dATP, dGTP, dCTP, and dTTP. The reversible terminator nucleotide used in this illustrative procedure included a 3'-ONH$_2$ reversible terminator moiety that was removable by contact with an acetate-buffered solution containing NaNO$_2$. A description of this reversible terminator nucleotide can be found in U.S. Pat. No. 7,544,794, the disclosure of which is incorporated herein by reference.

Multiple examination conditions were next screened using the immobilized beads attached to the blocked primed template nucleic acid molecules. Reversible terminator moieties on the 3' nucleotides of the primer strands precluded nucleotide incorporation during the ternary complex formation and detection steps. This allowed the same base position to be examined multiple times to determine which conditions supported specific formation and detection of ternary complex. Four different solutions that included a polymerase and a single nucleotide labeled on its base with a Cy5 moiety (i.e., Cy5-dATP, Cy5-dGTP, Cy5-dCTP, or Cy5-dTTP as described in U.S. patent application Ser. No. 15/873,343, which is incorporated herein by reference) were introduced to the flow cell individually to permit formation of ternary complexes.

After each nucleotide- and polymerase-containing solution was delivered to permit ternary complex formation, the flow cell was washed with imaging solution to remove non-complexed nucleotide and polymerase. Ternary complexes were detected during the imaging wash step. The solution (EXAM solution) providing polymerase and labeled nucleotide for formation of ternary complexes on the immobilized blocked primed template nucleic acid, and the imaging solution (IMG solution) both included 20 mM Tricine buffer (pH 8.42), 50 mM KCl, 0.1% Tween-80, 10 mM (NH$_4$)$_2$SO$_4$, and 3% sucrose. The solution used for forming ternary complexes further included 20 U/ml Therminator™ DNA polymerase (New England Biolabs; Ipswich, Mass.), 1 mM MgCl$_2$, and Cy5-dNTP (400 nM for each of Cy5-dATP, Cy5-dGTP, and Cy5-dCTP; 800 nM for Cy5-dTTP). The polymerase, MgCl$_2$, and nucleotides were omitted from the imaging fluid step. Each of the two solutions further included LiCl and/or betaine as stabilizing additives, where the solutions used in the same procedure contained like concentrations.

After imaging ternary complexes during the imaging wash step, polymerase and labeled nucleotide were stripped from the ternary complexes by washing the flow cell with a buffered EDTA-containing guanidinium thiocyanate solution. The flow cell was then prepared for the next base exam by flushing with pre-incorporation buffer (20 mM Tricine (pH 8.42), 50 mM KCl, 0.1% Tween-80, and 0.1% hydroxylamine). The EXAM and IMG solutions contained the same core ingredients, except that the imaging fluid did not include polymerase, MgCl$_2$ or labeled nucleotide. Variable conditions investigated in the procedure involved use of a lithium salt (i.e., LiCl) at either 5 mM or 50 mM, with or without 1 M betaine (N,N,N-trimethylglycine). Concentrations of LiCl and betaine used in the trials are summarized in Table 1. Results from these procedures are presented in FIGS. 1A and 1B.

TABLE 1

| Trial | Variable additions to EXAM and IMG |
|---|---|
| 1 | 0 mM LiCl; 0M Betaine |
| 2 | 5 mM LiCl; 0M Betaine |
| 3 | 50 mM LiCl; 0M Betaine |
| 4 | 0 mM LiCl; 1M Betaine |
| 5 | 5 mM LiCl; 1M Betaine |
| 6 | 50 mM LiCl; 1M Betaine |

FIG. 1A illustrates how lithium cations (e.g., resulting from dissolution of a lithium salt in water) and/or betaine advantageously increased fluorescent 'on' signals without raising fluorescent 'off' signals for each of the four tested nucleotides. The 'on' intensity is the median pixel count from an imaging camera of all correctly called nucleotides, and 'off' intensity is the median pixel count from the imaging camera for the remaining three nucleotides (i.e., the incorrect nucleotides) detected at the same features. Notably, the labeled dTTP nucleotide showed the greatest sensitivity to the different conditions, with the lowest 'on' signal being associated with complete absence of lithium cations and betaine. This trend was similar for all four nucleotides. Notably, while either of the tested concentrations of LiCl gave substantially saturating 'on' intensities, those results were further improved by the addition of betaine. This additive effect strongly suggested that lithium cations and betaine acted to improve the binding system via different mechanisms.

FIG. 1B graphically confirmed that higher confidence in correct base calling resulted from the use of lithium and betaine additives. Here purity values were calculated by dividing the brightest nucleotide intensity value by the sum of the brightest nucleotide intensity and the second brightest nucleotide intensity values. To display on a scale of 0 to 1, there is an adjustment to subtract 0.5 from the result, and then multiply by 2. As indicated, including lithium ions in the imaging solution used for detecting ternary complexes improved purity values, especially for the labeled dTTP nucleotide. In the absence of lithium, addition of betaine advantageously increased purity values for dTTP-ternary complexes.

Separate experiments (data not shown) demonstrated that increasing the LiCl concentration up to 100 mM, 175 mM or 250 mM also provided high 'on' signals indicating a stabilizing effect on ternary complexes. However, LiCl at 500 mM resulted in substantial reduction in 'on' signals and reduced purity, consistent with a destabilization of ternary complexes compared to the lower concentrations of LiCl.

These results demonstrate that lithium cations and betaine can provide ternary complex stabilization and can be included in an aqueous examination fluid to permit improved signal to noise ratio when detecting ternary complex in the presence of non-complexed labeled nucleotides.

EXAMPLE II

Stabilization of Ternary Complexes Over Time

This example describes a time titration that demonstrated improved detection of ternary complexes through washing with imaging buffer containing lithium and/or betaine for up to 5 minutes.

SBB™ reactions were conducted on blocked 3'-ONH$_2$ primed template DNA from 12 PCR reactions as set forth in Example I except that the extension step was omitted such that the same template position was repeatedly examined. Ternary complexes were allowed to form by flushing in EXAM solution as set forth in Example I. IMG solution was then introduced to the flow cell and flowed for either 20 seconds, 2½ minutes, or 5 minutes at a flow rate of 1 µL/s to wash off non-bound polymerase-nucleotide complexes prior to detection. The variable wash time and contents of IMG solution that was used for 15 examination cycles are shown in Table 2.

TABLE 2

| Cycle | Time  | LiCl  | Betaine |
|-------|-------|-------|---------|
| 1     | 20 s  | 50 mM | 1M      |
| 2     | 2.5 m | 50 mM | 1M      |
| 3     | 5 m   | 50 mM | 1M      |
| 4     | 20 s  | 0     | 0       |
| 5     | 2.5 m | 0     | 0       |
| 6     | 5 m   | 0     | 0       |
| 7     | 20 s  | 50 mM | 0       |
| 8     | 2.5 m | 50 mM | 0       |
| 9     | 5 m   | 50 mM | 0       |
| 10    | 20 s  | 0     | 1M      |
| 11    | 2.5 m | 0     | 1M      |
| 12    | 5 m   | 0     | 1M      |
| 13    | 20 s  | 50 mM | 1M      |
| 14    | 2.5 m | 50 mM | 1M      |
| 15    | 20 s  | 50 mM | 1M      |

As shown in FIG. 2, lithium (50 mM) and betaine (1M) provided increased 'on' signal intensity for the ternary complexes, shown in cycles 1-3 and 13-15. In the absence of lithium and betaine, ternary complexes dissociated and the ability to accurately discriminate correct bases was eliminated (shown in cycles 4-6). The addition of 50 mM lithium (cycles 7-9) permitted sequencing, but further addition of 1M betaine in combination with 50 mM lithium (cycles 1-3 and 13-15) showed a synergistic effect, greatly enhanced overall quality.

The results of FIG. 2 demonstrate that betaine helped for a short duration in stabilizing ternary complex, but after 2½ minutes all ternary complexes dissociated (cycle 11). There was a linear decay noted with overall intensities over the time points of 20 seconds, 2½ minutes and 5 minutes, but as demonstrated by the results shown in FIG. 3 purity values remained high and 'on' intensities were satisfactory for sequencing. The data collected showed that 50 mM LiCl and 1 M Betaine provided ternary complex stabilization over time.

Figure 4B:
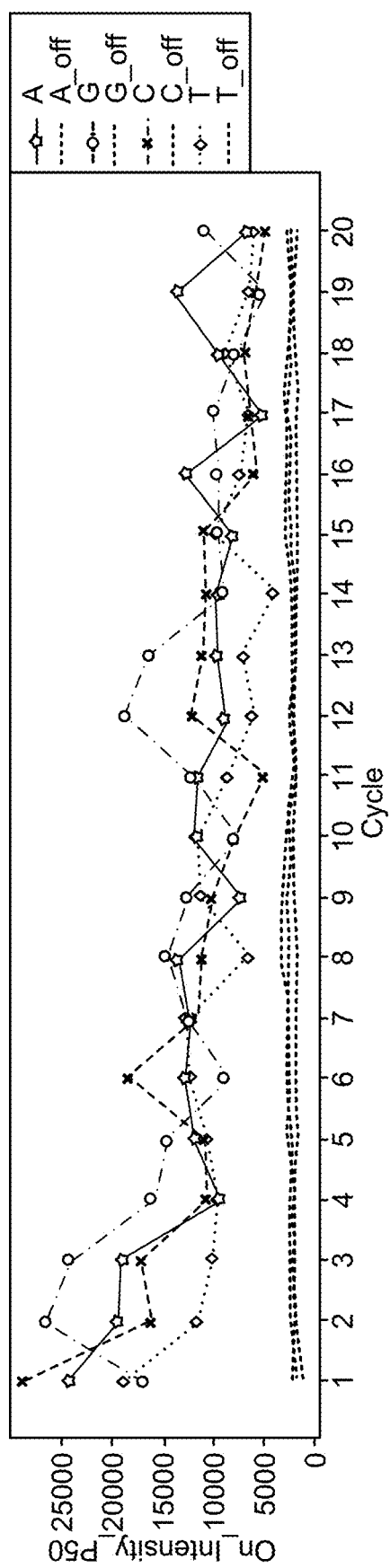
FIG. 4B shows a plot of 'on' and 'off' signal intensities for four different base types over 20 sequencing cycles carried out in the presence of 5 mM LiCl.
Figure 5A:
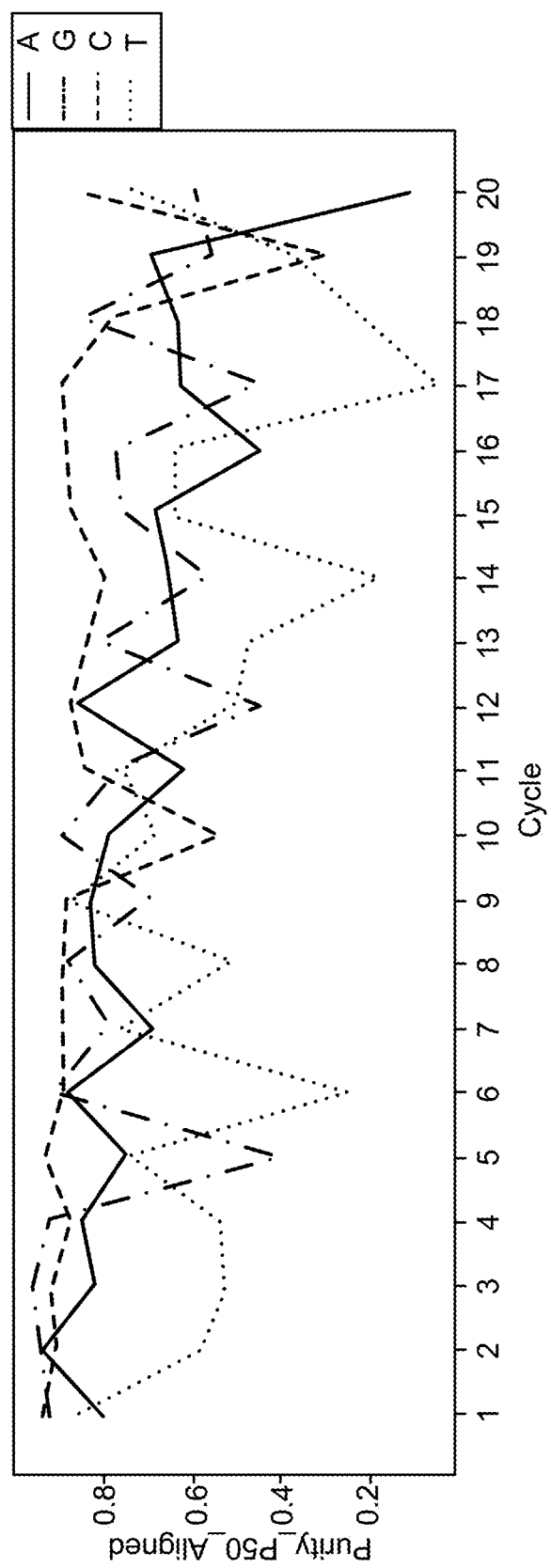
FIG. 5A shows a plot of purity for four different base types over 20 sequencing cycles carried out in the absence of LiCl.
Figure 5B:
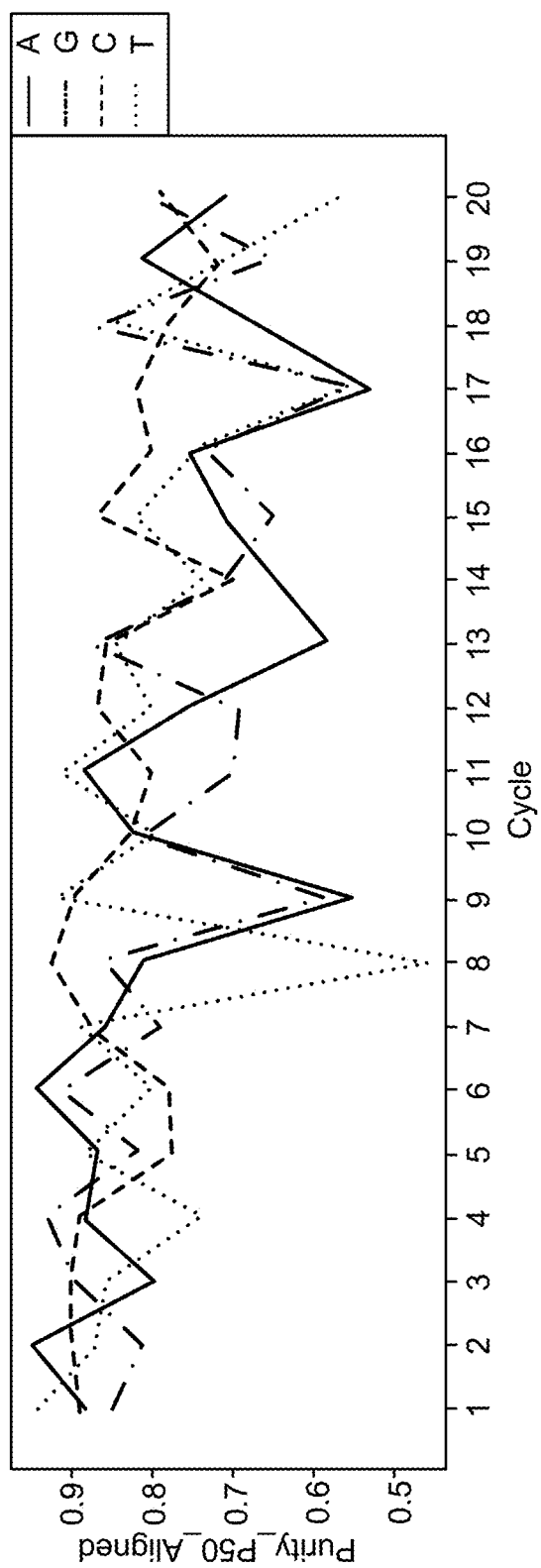
FIG. 5B shows a plot of purity for four different base types over 20 sequencing cycles carried out in the presence of 5 mM LiCl.
Figure 6A:
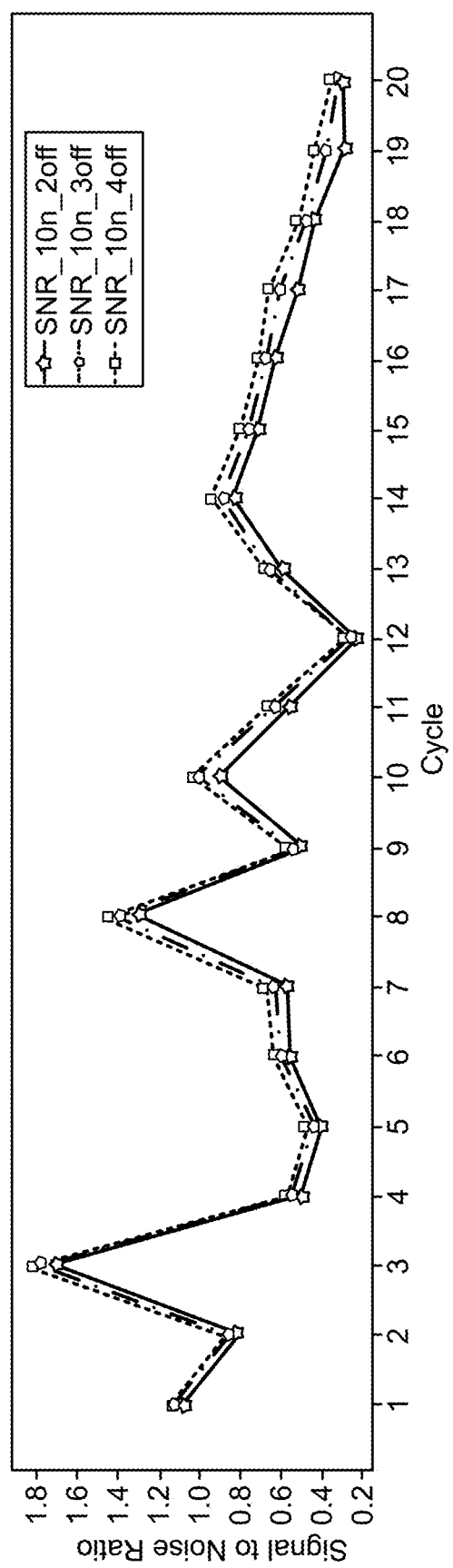
FIG. 6A shows a plot of signal to noise ratio over 20 sequencing cycles carried out in the absence of LiCl.
Figure 6B:
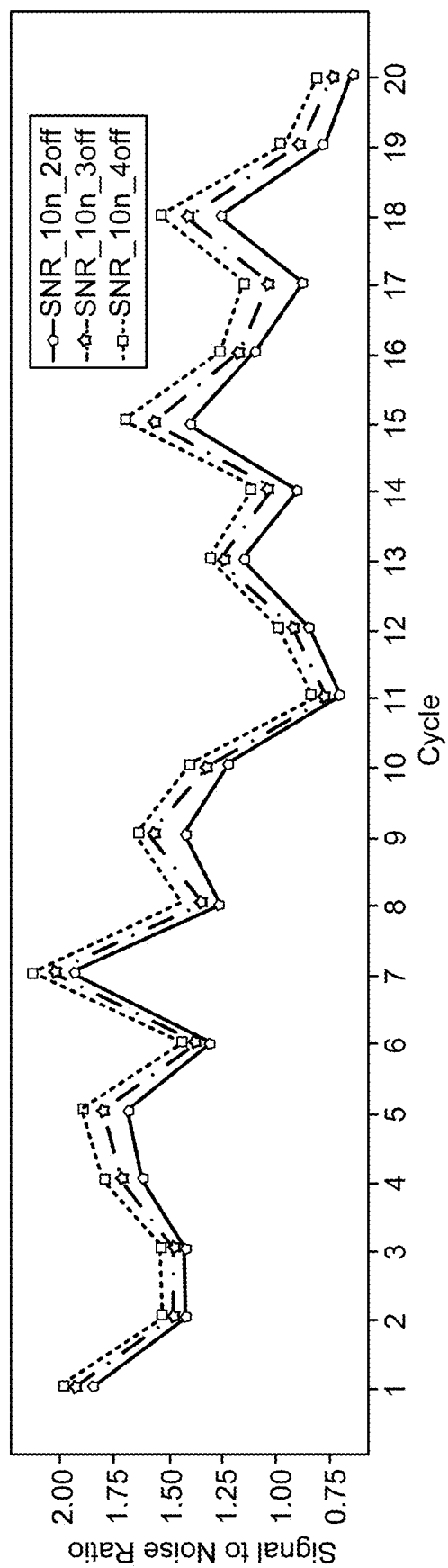
FIG. 6B shows a plot of signal to noise ratio over 20 sequencing cycles carried out in the presence of 5 mM LiCl.
Figure 6C:
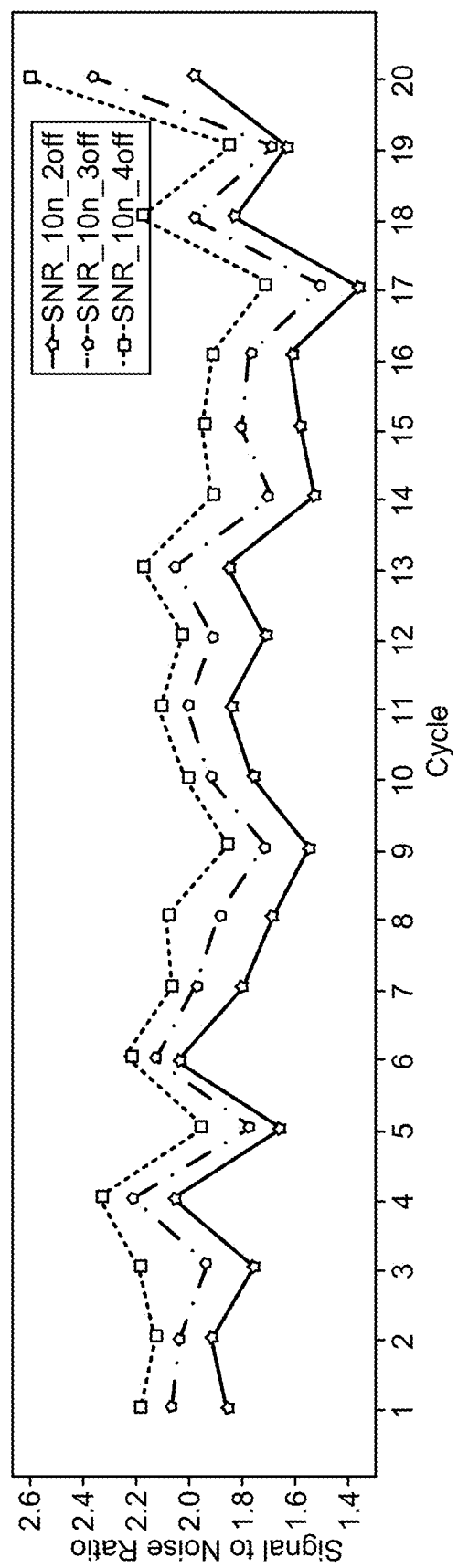
FIG. 6C shows a plot of signal to noise ratio over 20 sequencing cycles carried out in the presence of 50 mM LiCl.
Figure 7A:
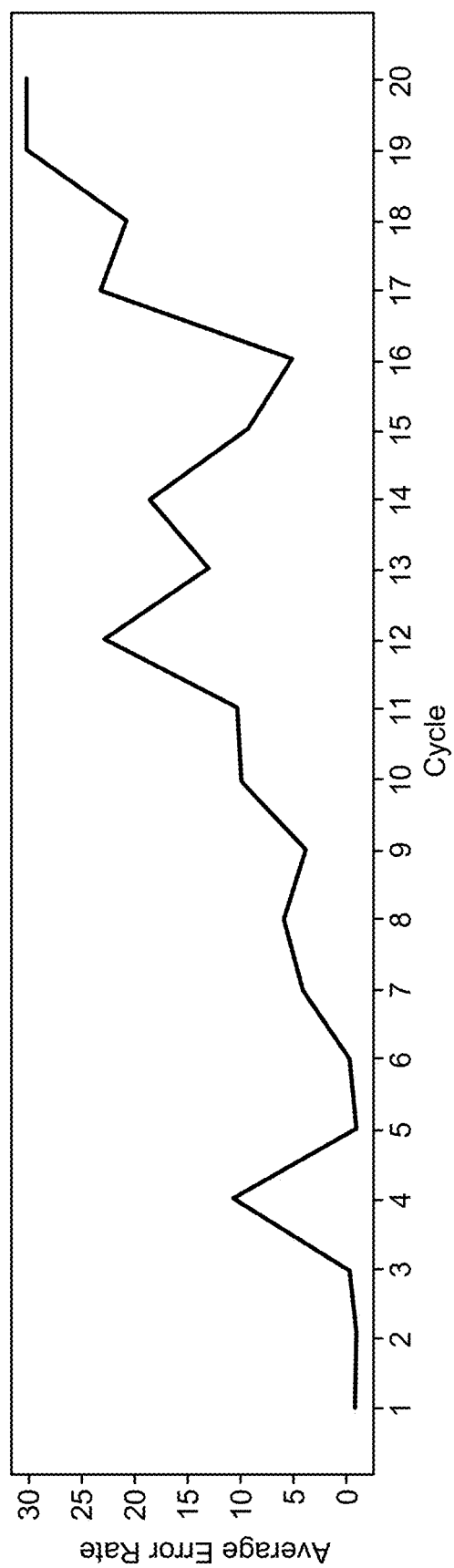
FIG. 7A shows a plot of average error rate over 20 sequencing cycles carried out in the absence of LiCl.
Figure 7C:
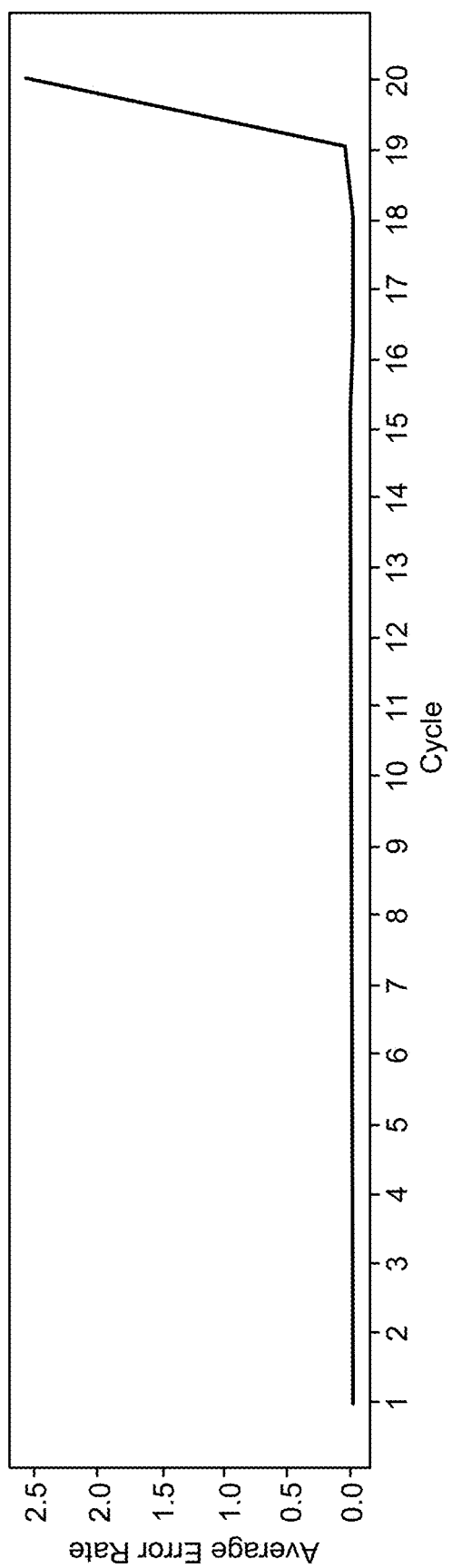
FIG. 7C shows a plot of average error rate over 20 sequencing cycles carried out in the presence of 50 mM LiCl.

Sequencing reactions were conducted with 0 mM, 5 mM and 50 mM LiCl and their qualities were observed over the course of 20 cycles. Betaine was present in all conditions at a concentration of 1 M. The results shown in FIGS. 4A through 4C demonstrate that increasing concentration of LiCl, up to 50 mM, increased separation between "on" and "off" signals and produced more uniform intensities over 20 cycles. The 'on' intensities were higher with 50 mM LiCl than 5 mM LiCl suggesting that the additional lithium aided in forming and stabilizing a greater population of ternary complexes. FIGS. 5A through 5C show that purities were higher with increased concentration of LiCl. Signal to noise ratio (SNR) also improved with increasing LiCl concentration up to 50 mM as demonstrated by the results shown in FIGS. 6A through 6C. Average error rates were also lower as the concentration of LiCl increased to 50 mM, as shown in FIGS. 7A through 7C.

EXAMPLE III

Stabilizing Ternary Complexes with an Aqueous Stabilizing Fluid that Contains Lithium, Calcium or Betaine This example demonstrates the effects of various combinations of lithium, Calcium and betaine on the stability of ternary complexes during SBB™ examinations steps.

SBB™ reactions were conducted in flow cells on blocked 3'-ONH$_2$ primed template DNA from 12 PCR reactions as set forth in Example I except that the extension step was omitted such that the same template position was repeatedly examined and the following modifications were made. The EXAM solution contained 20 mM Tricene pH 7.0, 3% sucrose, 50 mM KCl, 10 mM NH$_4$(SO)$_2$, 0.1% hydroxylamine, 0.1 mM EDTA, 0.1% Tween-80, 1 mM MgCl$_2$, 20 U/ml Therminator™ DNA polymerase, and Cy5-dNTP (400 nM for each of Cy5-dATP, Cy5-dGTP, and Cy5-dCTP; 800 nM for Cy5-dTTP). The IMG solution contained 20 mM Tricene pH 7.0, 3% sucrose, 50 mM KCl, 10 mM NH$_4$(SO)$_2$, 0.1% hydroxylamine, 0.1 mM EDTA, 0.1% Tween-80. Each of the solutions further contained variable additives as indicated in the tables below.

Ternary complexes were formed by flowing the EXAM solution into flow cells containing the DNA beads. Flow cells were then flushed with 16 µl of IMG solution for 16 seconds. Following the IMG flush, a first image of the DNA beads in the flow cell was acquired. After a delay of 60 seconds, a second image of the beads was acquired from the flow cell. The intensity of 'on' and 'off' signals were compared between the two images to determine ternary complex stability.

Table 3 shows variable contents for 8 examinations that optionally included lithium, calcium or betaine.

TABLE 3

| Cycle | Variable additives to EXAM and IMG           |
|-------|-----------------------------------------------|
| 1     | 1M Betaine; 50 mM LiCl; 0 mM CaCl$_2$         |
| 2     | 0M Betaine; 0 mM LiCl; 0 mM CaCl$_2$          |
| 3     | 0M Betaine; 50 mM LiCl; 0 mM CaCl$_2$         |
| 4     | 1M Betaine; 0 mM LiCl; 0 mM CaCl$_2$          |
| 5     | 0M Betaine; 0 mM LiCl; 0.5 mM CaCl$_2$        |
| 6     | 1M Betaine; 0 mM LiCl; 0.5 mM CaCl$_2$        |
| 7     | 0M Betaine; 50 mM LiCl; 0.5 mM CaCl$_2$       |
| 8     | 1M Betaine; 50 mM LiCl; 0.5 mM CaCl$_2$       |

Figure 8:
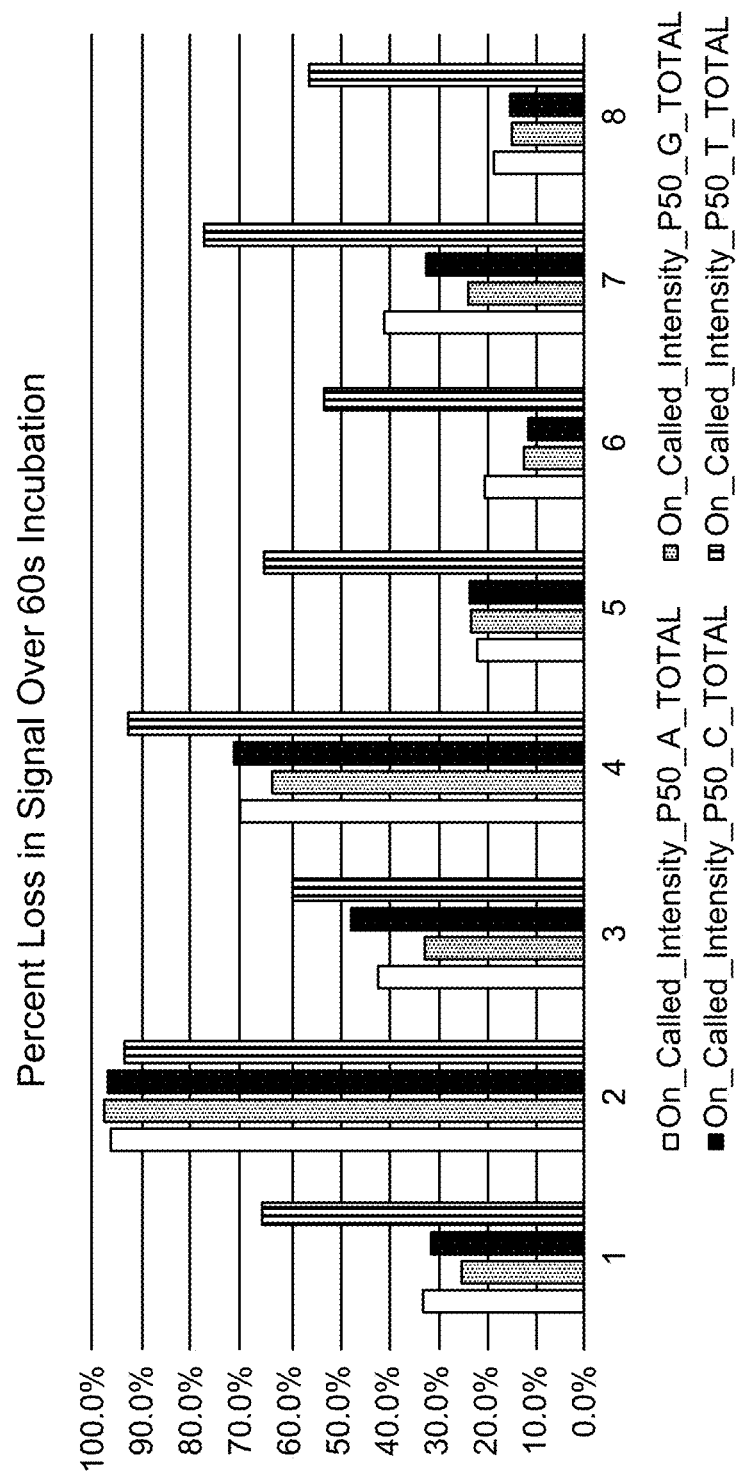
FIG. 8 shows percent loss in signal intensity for ternary complexes after 60 seconds in the presence of varying combinations of Lithium, Calcium or betaine.

The percent loss in signal intensity (from the first image to the second image) for each cycle is shown in FIG. 8. The percent loss for signals from ternary complexes formed in the presence of the four different cognate nucleotide types are indicated with individual bars (open bars for dATP, dotted bars for dGTP, solid bars for dCTP and hatched bars for dTTP). The most drastic signal loss (i.e. lowest stability) was seen for ternary complexes incubated in the absence of betaine, Calcium and Lithium (see cycle 2). The addition of 1 M betaine had a moderate effect on stabilizing ternary complexes formed with dATP, dGTP and dCTP, but did not appear to stabilize ternary complexes formed with dTTP (see cycle 4). The addition of 50 mM LiCl alone (see cycle 3) improved stability and further increase in stability was observed for ternary complexes formed with dATP, dGTP and dCTP when both 1M betaine and 50 mM LiCl were present (see cycle 1). The combination of betaine and lithium also had a stabilizing effect on ternary complexes formed with dTTP, albeit less pronounced than for the other three nucleotide types.

Continuing with the results in FIG. 8, the addition of 0.5 mM CaCl$_2$ alone (see cycle 5) resulted in an even greater increase in stability for ternary complexes formed with dATP, dGTP and dCTP, compared to the results with Lithium alone. The presence of 1 M betaine and 0.5 mM CaCl$_2$ (see cycle 6) also stabilized ternary complexes, the stabilization being slightly better than observed for Calcium alone. The combination of 50 mM LiCl and 0.5 mM CaCl$_2$ (see cycle 7) had a stabilizing effect on ternary complexes, especially complexes formed with dATP, dGTP and dCTP. The presence of all three additives, 1M betaine, 50 mM LiCl and 0.5 mM CaCl$_2$ (see cycle 8) also had a stabilizing effect on ternary complexes, especially complexes formed with dATP, dGTP and dCTP.

Figure 9:
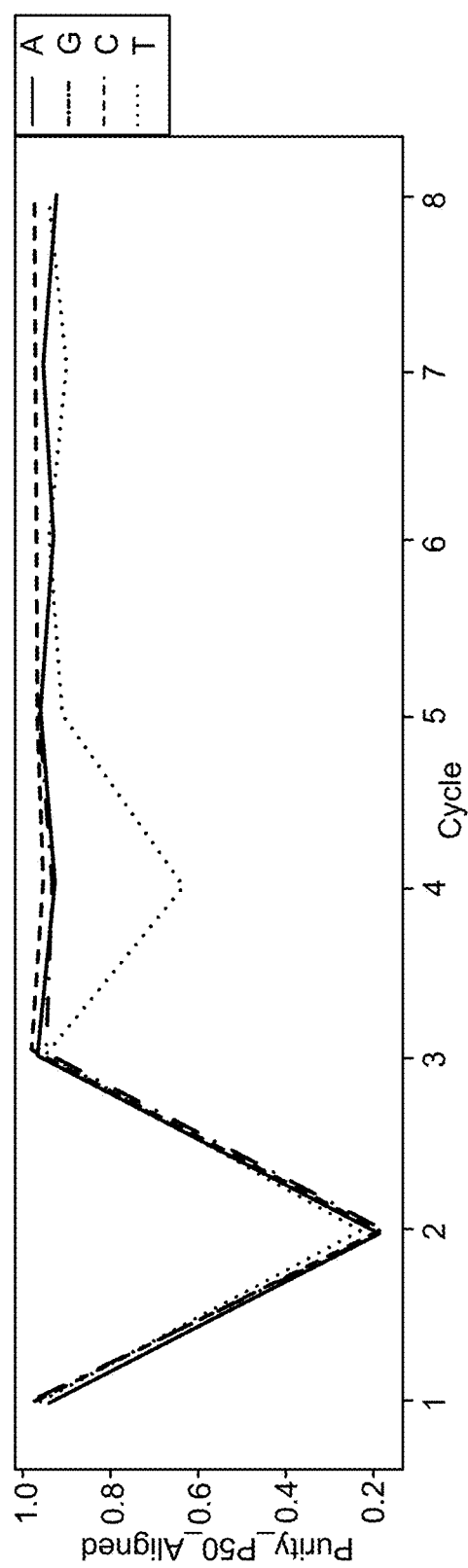
FIG. 9 shows a plot of purity values for sequencing cycles run in the presence of varying combinations of Lithium, Calcium or betaine.

FIG. 9 shows purity values obtained from the second images (i.e. after 60 second incubation in IMG solution). Cycle 2, run in the absence of lithium, betaine or calcium had the lowest purity scores, indicating dissociation of the ternary complexes. The addition of betaine alone resulted in low purity values for ternary complexes formed with dTTP. Cycles carried out in the presence of lithium (with or without betaine) or calcium (with or without betaine) produced complexes having high purity.

These results demonstrated that the presence of betaine, lithium or calcium during ternary complex formation and examination improved detection results, most likely by stabilizing ternary complexes. Independently, lithium and calcium appeared to be most effective. Addition of betaine to lithium or calcium had a synergistic effect in improving results. Ternary complexes formed with dATP, dGTP and dCTP were stabilized more significantly under most conditions tested compared to complexes formed with dTTP. Nevertheless, ternary complexes formed with dTTP appeared to be stabilized by betaine or lithium, alone or in combinations with betaine.

Several other metals were evaluated for their potential to stabilize ternary complexes in EXAM and IMG solutions. Doubling the concentration of KCl to 100 mM potassium or adding 50 mM sodium can be used when detecting ternary complexes, but ternary complexes, especially those formed with Cy5-dTTP were less stable than in the presence of similar concentrations of lithium or calcium. Strontium (10 mM SrCl$_2$) provided some stability to ternary complexes formed with purine nucleotides (Cy5-dATP and Cyl5-dGTP) but provided little to no stability to ternary complexes formed with pyrimidine nucleotides in the conditions tested. Nickel (2.5 mM NiSO$_4$) and Ytterbium (YbCl$_3$) did not provide very effective stabilization to ternary complexes in the conditions tested.

EXAMPLE IV

Stabilizing Ternary Complexes with Polyethylenimine

SBB™ reactions were conducted on blocked 3'-ONH$_2$ primed template DNA from 12 PCR reactions as set forth in Example I, and with the following modifications. The IMG solution included 20 mM Tricine buffer (pH 8.42), 50 mM KCl, 0.1% Tween-80, 10 mM (NH$_4$)$_2$SO$_4$, and 3% sucrose along with variable added reagents as set forth below. The EXAM solution included the same fixed and variable reagents as the IMG solution and further included 20 U/ml Therminator™ DNA polymerase (New England Biolabs; Ipswich, Mass.), 1 mM MgCl$_2$, and Cy5-dNTP (400 nM for each of Cy5-dATP, Cy5-dGTP, and Cy5-dCTP; 800 nM for Cy5-dTTP).

TABLE 4

| Condition | Variable additives to EXAM and IMG |
| --- | --- |
| SOP | No variable additives |
| 0.001 | 0.001% branched PEI 25k |
| 0.01 | 0.01% branched PEI 25k |
| 0.1 | 0.1% branched PEI 25k |
| 1.0 | 1.0% branched PEI 25k |

SBB™ reactions were run under the conditions that include variable additives to IMG and EXAM as specified in Table 4. In all conditions, the beads produced signals indicative of the formation of stabilized ternary complexes. However, it was observed that as the concentration of PEI increased, the ability to remove PEI and ternary complex from the beads via the standard wash protocol was decreased. High salt washes (4M NaCl) were effective at removing most of the PEI and base discrimination was possible after removal of PEI by high salt wash. However, higher background was observed after removal of PEI by high salt wash compared to the background for the SOP condition (i.e. no PEI, standard wash). Heparin was also found to be an effective agent for washing away PEI. Following the use of EXAM and IMG solutions having 0.001% 2k branched PEI, the PEI could be removed using wash solution that contained at least 30 µg/ml heparin (wash solutions having up to 100 µg/ml heparin were tested and found to be effective).

Figure 10:
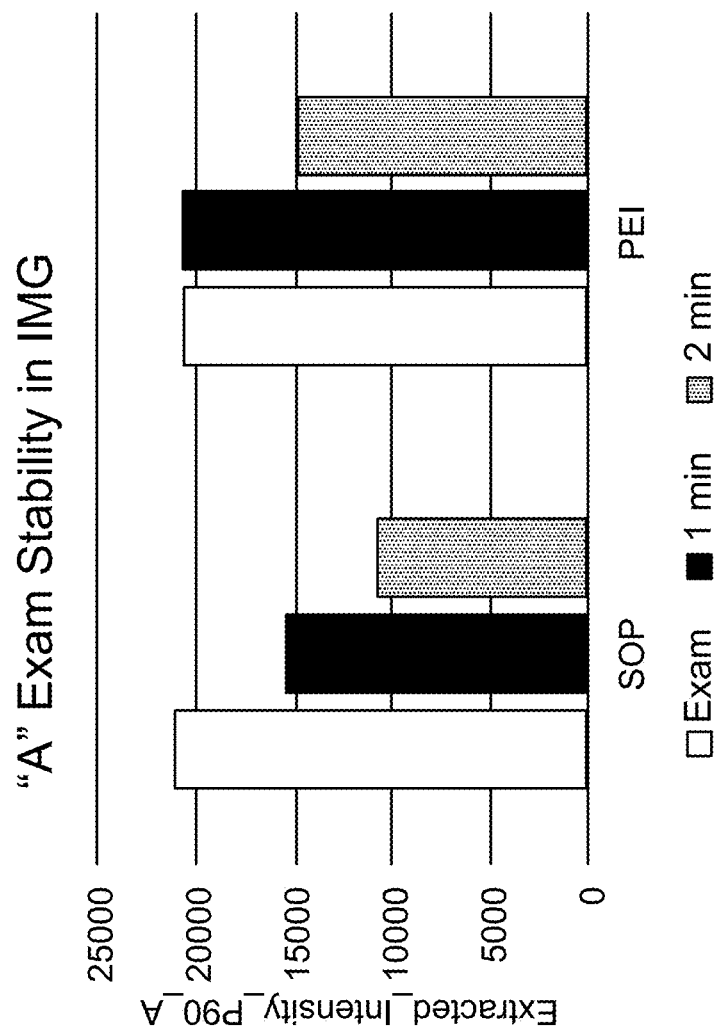
FIG. 10 shows the results of a stability test for ternary complexes in the presence and absence of PEI.

FIG. 10 shows the results of a stability test carried out as follows. Examination and imaging steps were carried out for beads having a primed-template with T as the next template nucleotide. For one lane of the flow cell, the Exam and IMG buffers included 0.001% branched PEI 25k (labeled as "PEI" in FIG. 10). A control lane was processed in parallel but lacked the added PEI (labeled as "SOP" in FIG. 10). The imaging step was modified such that a standard image was obtained (labeled "Exam" in FIG. 10), the beads were incubated in the dark for 1 minute and a second image was obtained ("1 min" in FIG. 10), and then the beads were incubated for another 1 minute before taking a third image ("2 min" in FIG. 10). As is evident from the results of FIG. 10, the presence of PEI provided a significant improvement in stability of the ternary complex across the three imaging timepoints.

Figure 11:
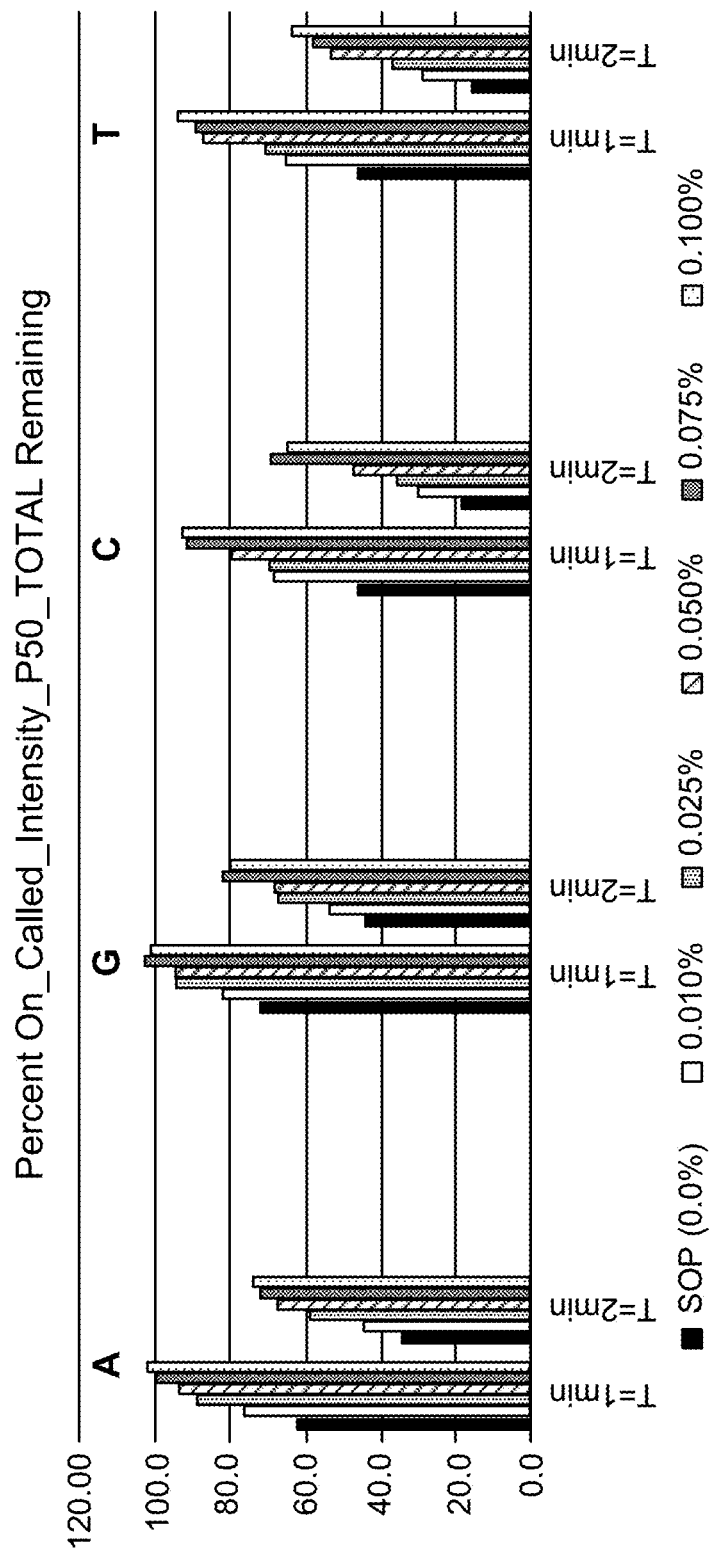
FIG. 11 shows the results of a stability test for ternary complexes in the presence of different concentrations of PEI.

FIG. 11 shows the results of stability tests carried out as follows. Examination and imaging steps were carried out for beads having a variety of primed-templates. The beads were distributed into 6 different lanes of a flow cell. The 6 flow cell lanes were processed in parallel but the EXAM and IMG solutions used for each lane differed as follows: no added PEI (SOP), 0.01% branched PEI 800, 0.025% branched PEI 800, 0.05% branched PEI 800, 0.075% branched PEI 800, 0.1% branched PEI 800. The imaging step was modified such that a standard image was obtained, the beads were incubated in the dark for 1 minute and a second image was obtained ("T=1 min" in FIG. 11), and then the beads were incubated for another 1 minute before taking a third image ("T=2 min" in FIG. 11). The data obtained from several different bead types was averaged such that all beads that produced a signal indicative of dATP as next correct nucleotide were averaged for the bars labeled A; all beads that produced a signal indicative of dGTP as next correct nucleotide were averaged for the bars labeled G; all beads that produced a signal indicative of dCTP as next correct nucleotide were averaged for the bars labeled C; and all beads that produced a signal indicative of dTTP as next correct nucleotide were averaged for the bars labeled T in FIG. 11. As is evident from the results, branched PEI 800 provided improved stability especially as the concentration approached or exceeded 0.075%.

Washes that included 40 µg/ml to 100 µg/ml heparin were effective at removing branched PEI 800 and ternary complexes from DNA beads (following delivery of EXAM and IMG having 0.1% branched PEI 800). Washes that included 100 µM to 1 mM sodium hexametaphosphate were effective at removing branched PEI 800 and ternary complexes from DNA beads (following delivery of EXAM and IMG having 0.075% branched PEI 800).

The results of this Example demonstrated that polyethylenimine can stabilize ternary complexes. Larger PEI molecules were effective at lower concentrations compared to smaller PEI molecules. However, larger PEI molecules are more difficult to remove from DNA beads than smaller PEI molecules. Smaller PEI molecules can be stripped from DNA beads with heparin and hexametaphosphate.

Throughout this application various publications, patents and/or patent applications have been referenced. The disclosures of these documents in their entireties are hereby incorporated by reference in this application.

A number of embodiments have been described. Nevertheless, it will be understood that various modifications may be made. Accordingly, other embodiments are within the scope of the following claims.

What is claimed is:

1. A composition, comprising a fluid, the fluid comprising a ternary complex and $Li^+$, wherein the ternary complex comprises a primed template nucleic acid molecule, a polymerase, and a nucleotide cognate for the next correct base for the primed template nucleic acid molecule, wherein the fluid further comprises free nucleotide at a concentration that is lower than the concentration of ternary complex in the fluid, the free nucleotide being the same type present in the ternary complex.

2. A method of detecting a primed template nucleic acid, comprising the steps of:
   (a) providing a fluid comprising a ternary complex and $Li^+$, wherein the ternary complex comprises a primed template nucleic acid molecule, a polymerase, and a nucleotide cognate for the next correct base for the primed template nucleic acid molecule;
   (b) detecting the ternary complex while it is in the fluid comprising $Li^+$;
   (c) identifying the next correct base for the primed template nucleic acid molecule from the result of step (b); and
   (d) extending the primer of the primed template nucleic acid, wherein the primer is extended by addition of a nucleotide comprising a reversible terminator moiety.

3. The method of claim 2, wherein the primer of the primed template nucleic acid molecule comprises a reversible terminator moiety.

4. The method of claim 3, further comprising (d) modifying or removing the reversible terminator moiety to deblock the primer.

5. The method of claim 4, further comprising (e) extending the deblocked primer by addition of a nucleotide comprising a reversible terminator moiety.

6. The method of claim 2, wherein ternary complex is immobilized on a solid support.

7. The method of claim 2, wherein the nucleotide cognate comprises an exogenous label that is detected in step (b).

8. The method of claim 7, wherein the mixture comprises nucleotide cognates for at least two different base types suspected of being present in the template nucleic acid.

9. The method of claim 8, wherein the nucleotide cognates for the different base types comprise different exogenous labels, respectively.

10. The method of claim 2, wherein the polymerase comprises an exogenous label that is detected in step (c).

11. The method of claim 2, wherein the fluid further comprises free nucleotide at a concentration that is lower than the concentration of ternary complex in the fluid, the free nucleotide being the same type present in the ternary complex.

12. The method of claim 2, wherein the fluid further comprises free polymerase at a concentration that is lower than the concentration of ternary complex in the fluid, the free polymerase being the same type present in the ternary complex.

13. The method of claim 2, wherein the fluid further comprises betaine.

14. The method of claim 2, wherein the fluid further comprises polyethylenimine.

15. A composition, comprising a fluid, the fluid comprising a ternary complex and $Li^+$, wherein the ternary complex comprises a primed template nucleic acid molecule, a polymerase, and a nucleotide cognate for the next correct base for the primed template nucleic acid molecule, wherein the fluid further comprises free polymerase at a concentration that is lower than the concentration of ternary complex in the fluid, the free polymerase being the same type present in the ternary complex.

* * * * *